(12) United States Patent
Tang et al.

(10) Patent No.: US 12,112,104 B2
(45) Date of Patent: Oct. 8, 2024

(54) SIMULATION ANALYSIS SYSTEM AND METHOD FOR DIOXIN CONCENTRATION IN FURNACE OF MUNICIPAL SOLID WASTE INCINERATION PROCESS

(71) Applicant: BEIJING UNIVERSITY OF TECHNOLOGY, Beijing (CN)

(72) Inventors: Jian Tang, Beijing (CN); JiaKun Chen, Beijing (CN); Heng Xia, Beijing (CN); Junfei Qiao, Beijing (CN)

(73) Assignee: BEIJING UNIVERSITY OF TECHNOLOGY, Beijing (CN)

( * ) Notice: Subject to any disclaimer, the term of this patent is extended or adjusted under 35 U.S.C. 154(b) by 0 days.

(21) Appl. No.: 18/407,170

(22) Filed: Jan. 8, 2024

(65) Prior Publication Data
US 2024/0143872 A1    May 2, 2024

Related U.S. Application Data

(63) Continuation of application No. PCT/CN2023/091010, filed on Apr. 27, 2023.

(30) Foreign Application Priority Data

Jun. 8, 2022    (CN) .......................... 202210644816.2

(51) Int. Cl.
*G06F 30/20*    (2020.01)
*A62D 3/00*    (2007.01)
(Continued)

(52) U.S. Cl.
CPC .............. *G06F 30/20* (2020.01); *A62D 3/00* (2013.01); *G16C 20/30* (2019.02); *B09B 5/00* (2013.01); *F23G 2200/00* (2013.01)

(58) Field of Classification Search
CPC .. G06F 30/20; G06F 2119/08; G06F 2111/10; A62D 3/00; F23G 2200/00
(Continued)

(56) References Cited

U.S. PATENT DOCUMENTS

2024/0143872 A1*   5/2024   Tang ..................... G16C 20/30

FOREIGN PATENT DOCUMENTS

CN    109960873 A  *  7/2019  .......... G05B 13/027
CN    109978011 A  *  7/2019
(Continued)

OTHER PUBLICATIONS

International Search Report for PCT/CN2023/091010.
(Continued)

*Primary Examiner* — Mohammed Alam
(74) *Attorney, Agent, or Firm* — J.C. PATENTS

(57) ABSTRACT

A simulation analysis system for dioxin concentration in furnace of municipal solid waste incineration process includes an area division module, the area division module is connected with a numerical simulation module, the numerical simulation module is connected with a single-factor analysis module, the single-factor analysis module includes an orthogonal test analysis module, and the orthogonal test analysis module is connected with a control module; the area division module is used for dividing areas in the incinerator, the numerical simulation module is used for conducting modeling simulation on the divided areas, the single-factor analysis module is used for conducting single-factor analysis according to the output of the numerical simulation module, and the orthogonal test analysis module is used for conducting orthogonal test analysis according to the output of the numerical simulation module.

7 Claims, 14 Drawing Sheets

(51) Int. Cl.
*B09B 5/00* (2006.01)
*G16C 20/30* (2019.01)

(58) Field of Classification Search
USPC ............................................... 588/19; 703/12
See application file for complete search history.

(56) References Cited

FOREIGN PATENT DOCUMENTS

| CN | 111823530 A | | 10/2020 | |
|---|---|---|---|---|
| CN | 114186514 A | | 3/2022 | |
| CN | 114602303 A | * | 6/2022 | |
| CN | 115344982 A | * | 11/2022 | ............. G06F 30/20 |

OTHER PUBLICATIONS

"Numerical simulation of dioxin emission concentration during incineration of municipal solid waste stoker", Advances in Chemical Engineering, vol. 42, No. 2, Feb. 15, 2023, pp. 1061-1072.

* cited by examiner

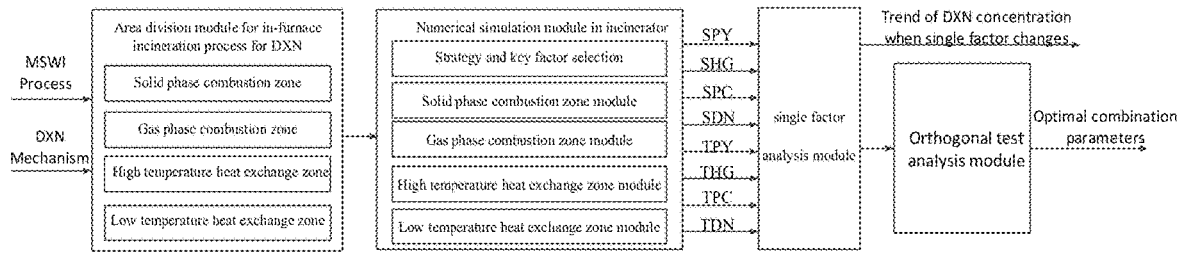

Fig. 1

Based on the MSWI process and the formation, decomposition and regeneration mechanism of DXN in the furnace, the furnace area of the incinerator is divided into solid phase combustion area, gas phase combustion area, high temperature heat exchange area and low temperature exchange area through the area division module According to the actual incinerator equipment parameters, operating parameters and boundary conditions, and the divided area, to simulate the numerical simulation model of the actual DXN emission value range through the data simulation module, and use the single factor analysis module to analyze SPY, SHG, SPC and SDN Single factor analysis of four streams;

Carry out multi-factor orthogonal test analysis through the orthogonal test analysis module according to the single factor analysis results and the data simulation module.

Fig. 2

SIMULATION ANALYSIS SYSTEM AND METHOD FOR DIOXIN CONCENTRATION IN FURNACE OF MUNICIPAL SOLID WASTE INCINERATION PROCESS

CROSS-REFERENCE TO RELATED APPLICATIONS

The present application is a continuation of the international application PCT/CN2023/091010 filed on Apr. 27, 2023, which claims the priority to the Chinese Patent Application No. 202210644816.2 filed on Jun. 8, 2022. The entire contents of the above identified applications are incorporated herein by reference.

TECHNICAL FIELD

The invention relates to the field of municipal solid waste incineration, in particular to a simulation analysis system and method for dioxin concentration in furnace of municipal solid waste Incineration process.

BACKGROUND

At present, MSW treatment methods include sanitary landfill, composting and incineration, among which MSW incineration (MSWI) technology has significant advantages in harmlessness, reduction and resource utilization, which is also the method vigorously promoted in China. However, the unstable MSWI process can produce dioxin-like (DXN) organic pollutants, including polychlorinated dibenzo-p-dioxins (PCDDs) and polychlorinated dibenzofurans (PCDFs). The persistent pollution of DXN will cause great harm to the environment and human health. Therefore, the research on the formation mechanism and inhibition technology of DXN for MSWI process has always been a hot issue in industry and academia.

The DXN generation process for MSWI process is very complicated, and its mechanism has not been fully understood so far, and further in-depth research and discussion are still needed. In view of the above reasons, at present, researchers mostly analyze the MSWI process through numerical simulation models to understand the incineration mechanism and optimize the design. At present, the detection and modeling of DXN is mainly aimed at the G3 flue gas discharged from the chimney, and fails to pay attention to the G1 flue gas at the outlet of the waste heat boiler, which is directly related to the generation of DXN. Therefore, it is necessary to design a simulation analysis system and method for dioxin concentration in the furnace during solid waste incineration to simulate and analyze the G1 flue gas at the outlet of the waste heat boiler.

SUMMARY

The purpose of the present invention is to provide a simulation analysis system and method for dioxin concentration in furnace of municipal solid waste Incineration process, which can realize the effective analysis and simulation of the mechanism of DXN generation, combustion and regeneration in the MSWI process incinerator, and provide a reference for reducing DXN concentration at the outlet of waste heat boiler. To achieve the above object, the present invention provides the following scheme:

A simulation analysis system for dioxin concentration in furnace of municipal solid waste Incineration process, comprising: an area division module, a numerical simulation module, a single factor analysis module and an orthogonal test analysis module, the area division module is connected to the numerical simulation module, the numerical simulation module is connected to the single factor analysis module, the single factor analysis module includes the orthogonal test analysis module, the area division module is used to divide the furnace area of incinerator, and the numerical simulation module is used for modeling and simulating each divided area, the single factor analysis module is used for performing single factor analysis according to the output of numerical simulation module, and the orthogonal test analysis module is used for performing an orthogonal test according to the output of numerical simulation module analyze;

The numerical simulation module includes a solid phase combustion zone simulation model, a gas phase combustion zone simulation model, a high temperature heat exchange zone simulation model, and a low temperature heat exchange zone simulation model, the solid phase combustion zone simulation model is connected to the gas phase combustion zone simulation model, the gas phase combustion zone simulation model is connected to the high temperature heat exchange zone simulation model, and the high temperature heat exchange zone simulation model is connected to the low temperature heat exchange zone simulation model.

Optionally, the solid phase combustion zone simulation model, the gas phase combustion zone simulation model, the high temperature heat exchange zone simulation model, and the low temperature heat exchange zone simulation model are composed of RStoic module, RGibbs module, RYield module, Sep module, Fsplit module and Mixer module, wherein RStoic module comprises Dry module and Deacon module, and RGibbs module comprises CombustionA1-A10 module, CombustionB1-B10 module, CombustionC1-C10 module, CombustionD1-D10 module, Pyrolysis1-10 module, Homogeneous1-10 module, PrecursorCatalytic1-10 modules and DeNovo1-10 modules, the RYield module includes a DryGrate module, a BurnGrate1 module, a BurnGrate2 module and a BurnoutGrate module, the Sep module includes a Sep1-Sep10 module, the Fsplit module includes a Split1-Split21 module, and the Mixer module includes Mix1-Mix11 modules;

The Dry module is used to reduce the water content of MSW, the Deacon module is used to carry out Deacon reaction, and the CombustionA1-A10 module, CombustionB1-B10 module, CombustionC1-C10 module, CombustionD1-D10 module are used to carry out solid-phase combustion, producing DXN, the Pyrolysis1-10 module is used for gas phase combustion, decomposition DXN, the Homogeneous1-10 module is used for high temperature gas phase reaction, the PrecursorCatalytic1-10 module is used for precursor catalytic reaction, the DeNovo1-10 module for de novo synthesis reaction, the DryGrate module, BurnGrate1 module, BurnGrate2 module and BurnoutGrate module are used to convert MSW into identifiable conventional components, simulated volatile analysis, and the Sep1-Sep10 module is used for component separation, the Split1-Split21 modules are used to split streams and the Mix1-Mix11 modules are used to mix streams.

Optionally, the solid-phase combustion zone simulation model includes a Dry module, MSW is input into the Dry module, the Dry module is respectively connected to the Split1, Split2 and Split3 modules, and the Split1 module is respectively connected to the DryGrate module, BurnGrate1 module, BurnGrate2 module and BurnoutGrate module, the DryGrate module, BurnGrate1 module, BurnGrate2 module and BurnoutGrate module are respectively connected to Sep4, Sep5, Sep6 and Sep7 modules, the Split3 module is connected to the Dry module and the DryGrate module respectively, and the Split2 module is respectively Connect Sep4, Sep5, Sep6 and Sep7 modules, the DryGrate module connects the BurnGrate1 module through Sep1, the BurnGrate1 module connects the BurnGrate2 module through Sep2, the BurnGrate2 module connects the BurnoutGrate module through the Sep3 module, and the Sep4, Sep5, Sep6 and Sep7 modules are respectively connected to the CombustionA1-A10 module, CombustionB1-B10 module, CombustionC1-C10 module, CombustionD1-D10 module through the Split4, Split5, Split6, Split7 modules, the CombustionA1-A10 module, CombustionB1-B10 module, CombustionC1-C10 module, CombustionD1-D10 module are respectively connected to Mix5 module through Mix1, Mix2, Mix3 and Mix4 modules.

Optionally, the gas-phase combustion zone simulation model includes a Sep8 module, the Mix5 module is connected to the Sep8 module, and the Sep8 module is respectively connected to the Split8, Split9, Split11, Split13 modules and the Pyrolysis6 module, and the Split8 modules are respectively connect Split9, Split11, Split13 module and Pyrolysis6 module, Split9 module connects Split10 module and Pyrolysis6 module respectively, and wherein, the stream that Split9 module connects Split10 module is the contained DXN concentration after gas phase combustion zone reaction, which is recorded for SPY, the Split10 module is connected to the Pyrolysis1-5 module, the Split11 module is connected to the Split12 module and the Pyrolysis6 module, the Split12 module is connected to the Pyrolysis7-8 module, the Split13 module is connected to the Pyrolysis6 module and the Split14 module, and the Split14 module is connected to the Pyrolysis9-10 module, and the Pyrolysis1-5 module, the Pyrolysis6 module, the Pyrolysis7-8 module, and the Pyrolysis9-10 module are connected to the Mix6 module.

Optionally, the high temperature heat exchange zone includes a Sep9 module, the Mix6 module is connected to the Sep9 module, the Sep9 module is respectively connected to the Deacon module, the Split15 module and the Split16 module, and the Split15 module is respectively connected to the Deacon module and the Split16 module, wherein, the stream of the Split15 module connected to the Split16 module is the DXN concentration after the reaction in the high-temperature heat exchange zone, denoted as SHG, the Split16 module is connected to the Homogeneous1-10 module, and the Homogeneous1-10 module is connected to the Mix7 module, the Deacon module and the Mix7 module are connected to the Mix8 module.

Optionally, the low temperature heat exchange zone includes a Sep10 module, the Mix8 module is connected to the Sep10 module, the Sep10 module is respectively connected to the Split17 module, the Split19 module, the Split20 module and the Heater module, and the Split17 module is respectively connected to the Split18 module and the Heater module, the Split20 module is respectively connected to the Split21 module and the Heater module, the Split17 module is connected to the stream of the Split18 module, the Split20 module is connected to the stream of the Split21 module, which is the concentration of DXN after the reaction in the low temperature heat exchange zone, recorded as SPC and SDN, respectively, the Split19 module is connected to the Split18 module and the Split21 module, the Split18 module is connected to the PrecursorCatalytic1-10 module, the PrecursorCatalytic1-10 module is connected to the Mix9 module, and the Split21 module is connected to the DeNovo1-10 modules, the DeNovo1-10 module is connected to the Mix10 module, the Mix9 module, Mix10 module and Heater module are connected to the Mix11 module to output the DXN concentration at the boiler outlet.

The present invention also provides a simulation analysis method for dioxin concentration in furnace of municipal solid waste Incineration process, which is applied to the simulation analysis system for dioxin concentration in furnace of municipal solid waste Incineration process, including the following steps:

Step 1: Based on the MSWI process and the formation, decomposition and regeneration mechanism of DXN in the furnace, the furnace area of the incinerator is divided into solid phase combustion area, gas phase combustion area, high temperature heat exchange area and low temperature exchange area through the area division module.

Step 2: According to the actual incinerator equipment parameters, operating parameters and boundary conditions, and the divided area, to simulate the numerical simulation model of the actual DXN emission value range through the numerical simulation module, and use the single factor analysis module to analyze SPY, SHG, SPC and SDN Single factor analysis of four streams;

Step 3: Carry out multi-factor orthogonal test analysis through the orthogonal test analysis module according to the single factor analysis results and the numerical simulation module.

According to the specific embodiments provided by the present invention, the present invention discloses the following technical effects: the simulation analysis system and method for dioxin concentration in the furnace during the solid waste incineration process provided by the present invention, the system includes an area division module, a numerical simulation module, a unit factor analysis module and orthogonal test analysis module, this method includes based on the MSWI process and the formation, decomposition and regeneration mechanism of DXN in the furnace, and divides the furnace area of the incinerator into solid phase combustion area, gas phase combustion zone, high temperature heat exchange zone and low temperature heat exchange zone, based on the actual incinerator equipment parameters, operating parameters and boundary conditions, the divided areas are simulated through the numerical simulation model of the numerical simulation module in line with the actual DXN emission value range, the analysis module conducts single-factor analysis on the four streams of SPY, SHG, SPC and SDN, and conducts multi-factor orthogonal test analysis through the orthogonal test analysis module according to the single-factor analysis results and the numerical simulation module; Compared with the actual data, the results are basically consistent, indicating the effectiveness of the numerical simulation model, which can realize the effective analysis and simulation of the mechanism of DXN generation, combustion and regeneration in the MSWI process incinerator, in order to reduce the waste heat boiler outlet. DXN concentrations are provided for reference.

DESCRIPTION OF DRAWINGS

In order to more clearly illustrate the technical solutions in embodiments of the present invention or prior art, the following will briefly introduce the accompanying drawings required in the embodiments. Obviously, the accompanying drawings in the following description are only some of the embodiments, for those of ordinary skill in the art, other drawings can also be obtained according to these drawings without paying creative labor.

FIG. 1 is a schematic structural diagram of a simulation analysis system for dioxin concentration in furnace of municipal solid waste Incineration process according to an embodiment of the present invention;

FIG. 2 is a schematic flow chart of the simulation analysis system for dioxin concentration in furnace of municipal solid waste Incineration process according to the embodiment of the present invention;

PREFERRED EMBODIMENTS

The following will clearly and completely describe the technical solutions in the embodiments of the present invention with reference to the accompanying drawings. Obviously, the described embodiments are only some embodiments of the present invention. Based on the embodiments of the present invention, all other embodiments obtained by persons of ordinary skill in the art without making creative efforts belong to the protection scope of the present invention.

The purpose of the present invention is to provide a simulation analysis system and method for dioxin concentration in furnace of municipal solid waste Incineration process, which can realize the effective analysis and simulation of the mechanism of DXN generation, combustion and regeneration in the MSWI process, and provide a reference for reducing the DXN concentration at the outlet of the waste heat boiler.

In order to make the above objects, features and advantages of the present invention more comprehensible, the present invention will be further described in detail below in conjunction with the accompanying drawings and specific embodiments.

As shown in FIG. 1, the simulation analysis system and method for dioxin concentration in furnace of municipal solid waste Incineration process provided by the embodiment of the present invention includes: an area division module, a numerical simulation module, a single factor analysis module and an orthogonal test analysis module. The area division module is connected to the numerical simulation module, the numerical simulation module is connected to the single factor analysis module, the single factor analysis module includes a orthogonal test analysis module, and the area division module is used to divided the inner area of furnace of the incinerator, the numerical simulation module is used to model and simulate the divided areas, the single factor analysis module is used to perform single factor analysis according to the output of the numerical simulation module, and the orthogonal test analysis module is used for carrying out orthogonal test analysis according to the output of the numerical simulation module;

The numerical simulation module includes a solid phase combustion zone simulation model, a gas phase combustion zone simulation model, a high temperature heat exchange zone simulation model, and a low temperature heat exchange zone simulation model, the solid phase combustion zone simulation model is connected to the gas phase combustion zone simulation model, the gas phase combustion zone simulation model is connected to the high temperature heat exchange zone simulation model, the high temperature heat exchange zone simulation model is connected to the low temperature heat exchange zone simulation model.

Figure 8:
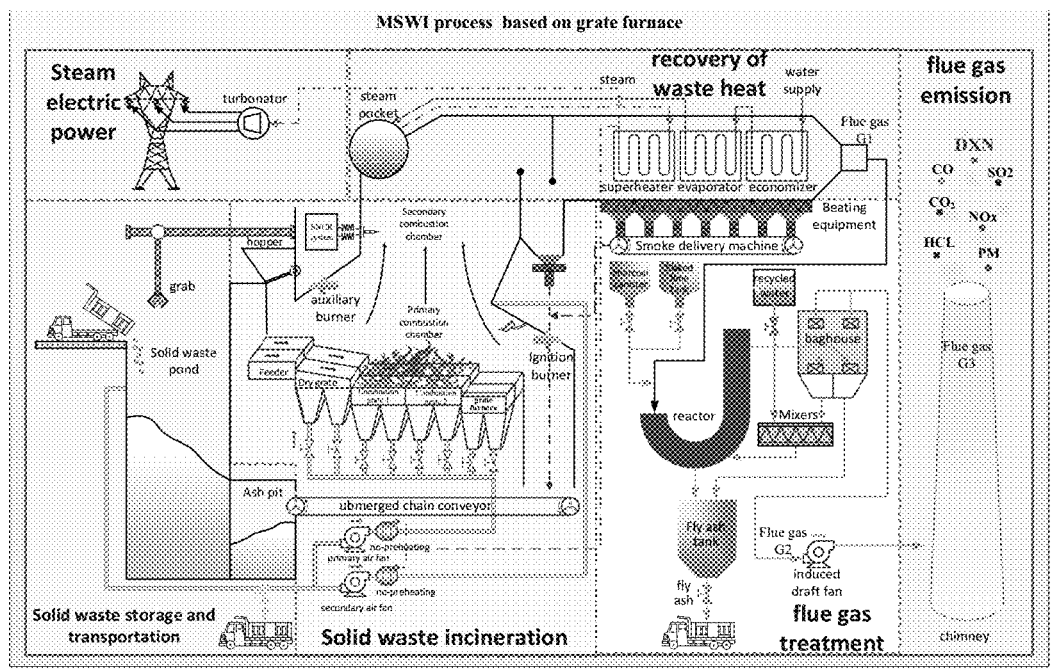
FIG. 8 is the MSWI process flow chart based on the grate furnace

As shown in FIG. 8, from the perspective of DXN concentration, there will be a trace amount of DXN (about 0.8 ng TEQ/Kg) in original MSW and contain various chlorine-containing compounds required for its formation, the feeder pushes the MSW into the incinerator, through drying, burning 1, burning 2 and burnout grate in order to make the combustible components burn, in order to ensure that the DXN contained in the original MSW and produced during solid phase combustion can be completely decomposed in the furnace, the gas phase combustion process needs to strictly control the flue gas temperature above 850° C., the high-temperature flue gas stays in furnace for more than 2 seconds, and ensure sufficient flue gas turbulence. The high-temperature flue gas generated in the furnace is sucked into the waste heat recovery system by the induced draft fan, high-temperature steam is generated after heat exchange with the liquid water in the boiler drum, and the flue gas temperature at the outlet of the waste heat boiler after the cooling treatment is lower than 200° C. (that is, the flue gas G1). The chemical processes that can generate DXN when the boiler cools down include high-temperature gas-phase synthesis (800° C.-500° C.), precursor synthesis (450° C.-200° C.) and de novo synthesis (350° C.-250° C.). According to the above description, the incinerator is divided into solid phase combustion zone, gas phase combustion zone, high temperature heat exchange zone and low temperature heat exchange zone.

Among them, the solid phase combustion zone: when MSW burns from the solid phase, the DXN contained in itself will be released, incomplete combustion products will be generated under the condition of local oxygen deficiency, which is the key precursor for the formation of DXN, mainly Including chlorobenzene, polychlorobenzene, chlorophenol, polycyclic aromatic hydrocarbons, etc. Further, the DXN generated by these precursors through chemical reactions enters the gas phase combustion zone in the furnace;

Gas-phase combustion zone: the temperature of the gas-phase combustion zone is 800-1000° C. The DXN and precursors volatilized and generated in the solid-phase combustion zone of the grate will be decomposed due to high-temperature combustion in this range, and the final products are $CO_2$ and HCl;

High-temperature heat exchange area: the temperature is between 800 and 500° C., which corresponds to the heat exchange area of the superheater for waste heat recovery, in which: because the reaction is dominated by high-temperature synthesis of gas-phase DXN, the content of solid-phase and liquid-phase DXN is very small, chlorine Phenol oxidative coupling is the main way to generate DXN, which can be divided into 3 steps of chlorophenoxy radical formation, coupling and cyclization from the mechanism;

Low-temperature heat exchange zone: the temperature is between 500° C. and 200° C., mainly for low-temperature heterogeneous catalytic reactions, including two types of catalytic reactions on the surface of precursors and de novo synthesis reactions.

When the precursors such as chlorophenol and chlorobenzene carried by the flue gas and decomposed by carbon residue are cooled, metals such as CuO are used as catalysts to generate PCDD/Fs according to the mechanism of ER and LH, which can be divided into catalysts adsorbed by precursors in fly ash, adsorption of the second precursor molecule, condensation of the adsorbed molecule to generate PCDD/Fs, and desorption of PCDD/Fs are four steps in total. The de novo synthesis reaction is based on carbon, and DXN is generated through a series of elementary reactions such as chlorination and oxidation. The necessary conditions are: the presence of organic or inorganic chlorine, the presence of oxygen, and the chlorides of transition metals as catalysts, and the residual carbon is adsorbed in the pores of fly ash particles.

Part of the PCDD/Fs produced by the above reactions will diffuse into the flue gas, but most of them remain in the fly ash. The influencing factors include: temperature, reaction time, residual carbon in fly ash, form and content of chlorine, catalyst, PH value and reaction atmosphere ($O_2$, $H_2O$, $Cl_2$, HCl), etc.

The systems and methods for realizing the present invention need to be in a steady-state environment, namely:

(1) The incinerator is in a stable operating state, the reaction in the furnace can reach equilibrium, the temperature and pressure in each reactor are constant and pressure loss and heat loss are not considered;
(2) During the incineration process, MSW and air are fully mixed and distributed evenly, and the influence of MSW particle size on combustion is ignored;
(3) The main elements of MSW are C, H, O, N, S and Cl, among which: H, O, N, S and Cl are all converted into the gas phase; part of C is converted into the gas phase, and part of it is converted into residual carbon and ash; As an inert substance, ash does not participate in any reaction;
(4) Because the tar component is extremely complex, it is assumed that the product does not contain tar.

As shown in FIG. 1, FIG. 3, FIG. 4, FIG. 5 and FIG. 6, the simulation model of the solid phase combustion zone, the simulation model of the gas phase combustion zone, the simulation model of the high temperature heat exchange zone, and the simulation model of the low temperature heat exchange zone are composed of the RStoic module, RGibbs module, RYield module, Sep module, Fsplit module and Mixer module, the RStoic module includes Dry module and Deacon module, the RGibbs module includes CombustionA1-A10 module, CombustionB1-B10 module, CombustionC1-C10 module, CombustionD1-D10 module, Pyrolysis1-10 module, Homogeneous1-10 module, PrecursorCatalytic1-10 module and DeNovo1-10 module, RYield module comprises DryGrate module, BurnGrate1 module, BurnGrate2 module and BurnoutGrate module, Sep module comprises Sep1-Sep10 module, Fsplit module comprises Split1-Split21 module, and Mixer module comprises Mix1-Mix11 module; The Dry module is used to reduce the water content of MSW, the Deacon module is used to carry out Deacon reaction, and the CombustionA1-A10 module, CombustionB1-B10 module, CombustionC1-C10 module, CombustionD1-D10 module are used to carry out solid-phase combustion to produce DXN, the Pyrolysis1-10 is used for gas phase combustion, decomposition DXN, the Homogeneous1-module is used for high temperature gas phase reaction, the PrecursorCatalytic1-10 module is used for precursor catalytic reaction, the DeNovo1-10 module is used for de novo synthesis reaction, the DryGrate module, BurnGrate1 module, BurnGrate2 module and BurnoutGrate module are used to convert MSW into identifiable conventional components, simulated volatile analysis, and the Sep1-Sep10 module is used for component separation, the Split1-Split21 modules are used to split streams and the Mix1-Mix11 modules are used to mix streams.

Figure 3:
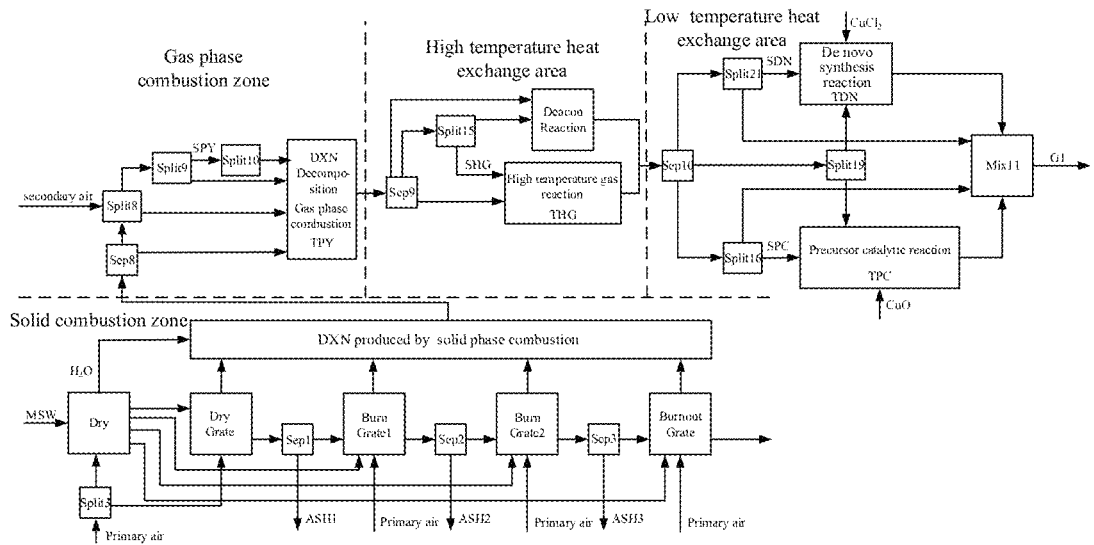
FIG. 3 is a structural diagram of the simulation strategy model.

As shown in FIG. 3, the simulation model of the solid-phase combustion zone includes a Dry module, and MSW is input into the Dry module, the Dry module is respectively connected to the Split1, Split2 and Split3 modules, and the Split1 module is connected to the DryGrate module, the BurnGrate1 module, BurnGrate2 module and BurnoutGrate module respectively, the DryGrate module, BurnGrate1 module, BurnGrate2 module and BurnoutGrate module are respectively connected to Sep4, Sep5, Sep6 and Sep7 modules, the Split3 module is respectively connected to the Dry module and the DryGrate module, the Split2 modules are respectively connected to Sep4, Sep5, Sep6 and Sep7 modules, the DryGrate module is connected to the BurnGrate1 module through Sep1, the BurnGrate1 module is connected to the BurnGrate2 module through Sep2, and the BurnGrate2 module is connected to the BurnoutGrate module through the Sep3 module, so the Sep4, Sep5, Sep6 and Sep7 modules are respectively connected to the CombustionA1-A10 module, the CombustionB1-B10 module, the CombustionC1-C10 module, and the CombustionD1-D10 module through the Split4, Split5, Split6, and Split7 modules, the CombustionA1-A10 module, CombustionB1-B10 module, CombustionC1-C10 module, and CombustionD1-D10 module are respectively connected to Mix5 module through Mix1, Mix2, Mix3 and Mix4 modules. Among them, Split3 module, BurnGrate1 module, BurnGrate2 module and BurnoutGrate module respectively input primary air, Sep1, Sep2, Sep3 module outputs ASH1, ASH2 and ASH3 respectively;

The MSW containing moisture first enters the Dry module for drying, and then flows into the DryGrate module, BurnGrate1 module, BurnGrate2 module and BurnoutGrate module respectively through the Split1 module to simulate volatile analysis, and the moisture enters the subsequent reaction, as shown in the formula:

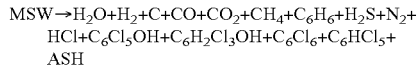

$$MSW \rightarrow H_2O + H_2 + C + CO_2 + CO_2 + CH_4 + C_6H_6 + H_2S + N_2 + HCl + C_6Cl_5OH + C_6H_2Cl_3OH + C_6Cl_6 + C_6HCl_5 + ASH$$

In the formula, $C_6Cl_5OH$ is pentachlorophenol, $C_6H_2Cl_3OH$ is 2,4,6-trichlorophenol, $C_6H_6$ is benzene, $C_6Cl_6$ is hexachlorobenzene, $C_6HCl_5$ is pentachlorobenzene, and ASH is ash;

Further, the volatile matter is separated by the Sep4-Sep7 module, and small amount HCl, CBz (chlorobenzenes) and CP (chlorophenols) are separated into the S30-S33 stream, and in the CombustionA1-A10, B1-B10, C1-C10 and D1-D10 consists of 4 groups of modules, and each group is equipped with 10 RGibbs reactors to simulate the process of solid-phase combustion to generate DXN. Among them, according to the number of Cl atom substitutions and PCDDs and PCDFs, 17 kinds of DXN congeners are divided into 10 types, respectively produced by the above-mentioned RGibbs reactor.

Figure 4:
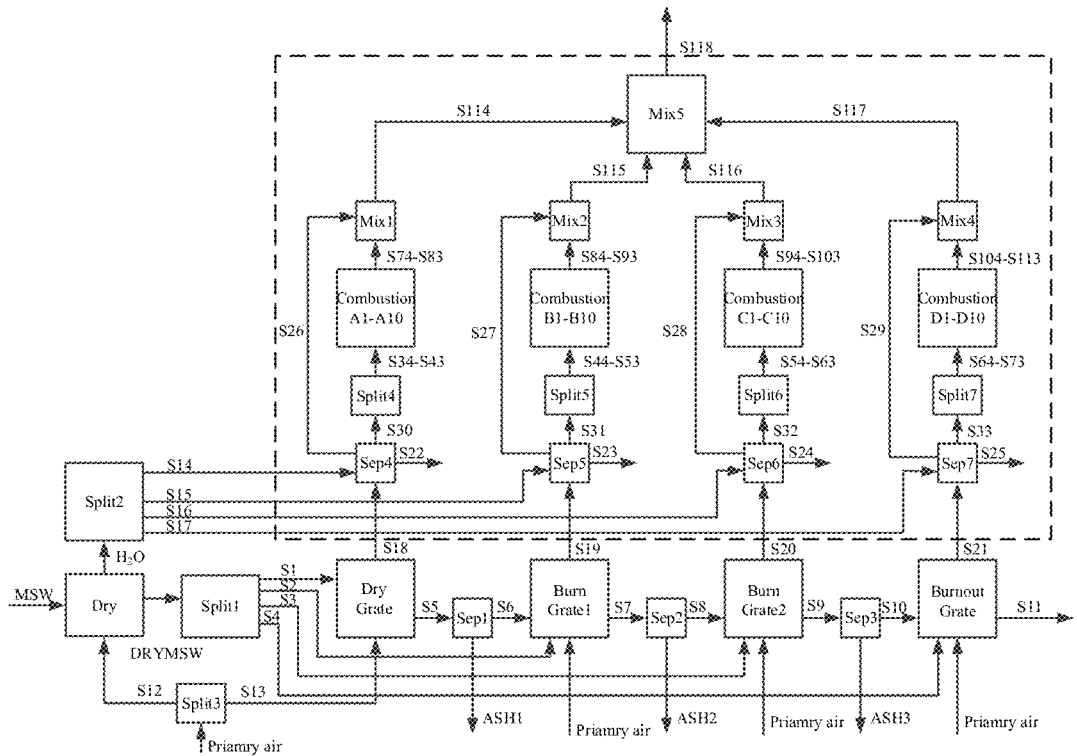
FIG. 4 is the structural diagram of the solid phase combustion zone simulation model.

As shown in FIG. 4, the simulation model of the gas-phase combustion zone includes a Sep8 module, the Mix5 module is connected to the Sep8 module, and the Sep8 module is respectively connected to the Split8, Split9, Split", Split13 modules and the Pyrolysis6 module, the Split8 modules are respectively connected to the Split9, Split11, Split13 modules and the Pyrolysis6 module, the Split9 module is connected to the Split10 module and the Pyrolysis6 module respectively, wherein the stream that Split9 module connected to the Split10 module is the concentration of DXN contained after the reaction in the gas phase combustion zone, recorded as SPY, the Split10 module is connected to the Pyrolysis1-5 module, the Split11 module is connected to the Split12 module and the Pyrolysis6 module, the Split12 module is connected to the Pyrolysis7-8 module, and the Split13 module is connected to the Pyrolysis6 module and the Split14 module. Split14 module connects Pyrolysis9-10 module, Pyrolysis1-5 module, Pyrolysis6 module, Pyrolysis7-8 module, Pyrolysis9-10 module connect Mix6 module, Split8 module flows into secondary air;

Stream S118 from the solid phase combustion zone separates DXN, HCl, CBz, and CP through Sep8 (the corresponding streams are recorded as S119, S121, S122, and S123, respectively). Correspondingly, DXN generates high temperature at the Pyrolysis1-Pyrolysis5 module decomposition and synthesis reactions, similar to the above, the 5 RGibbs modules will be set according to the number of Cl atom substitutions, the Pyrolysis6 module will perform the decomposition reactions of DXN, CBz and CP, the Pyrolysis7-8 modules will perform the decomposition and synthesis reactions of CBz, and the Pyrolysis9 and 10 module carries out the decomposition and synthesis reaction of CP, and SPY can characterize the concentration of DXN contained in the gas phase combustion zone after the reaction.

Figure 5:
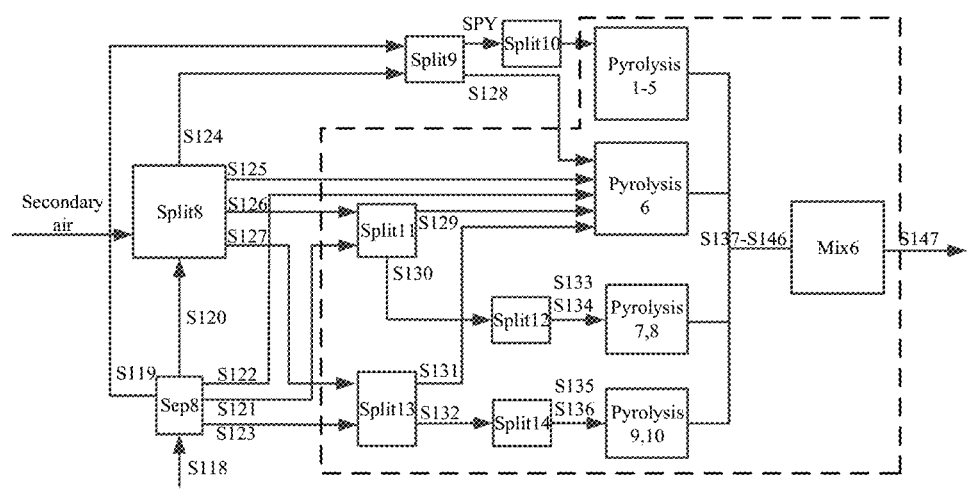
FIG. 5 is the structural diagram of the gas phase combustion zone simulation model.

As shown in FIG. 5, the high temperature heat exchange zone includes a Sep9 module, the Mix6 module is connected to the Sep9 module, the Sep9 module is connected to the Deacon module, the Split15 module and the Split16 module respectively, and the Split15 module is connected to the Deacon module and the Split16 module respectively. Wherein, the stream that Split15 module connected to the Split16 module is the DXN concentration after the high temperature heat exchange zone reaction, recorded as SHG, the Split16 module is connected to the Homogeneous1-10 module, and the Homogeneous1-10 module is connected to the Mix7 module, the Deacon module and the Mix7 module are connected to the Mix8 module;

Stream S147 from the gas phase combustion zone is divided into streams S148, S149 and S150 by Sep9; further, S149 is divided into streams S150 and SHG by Split15, and the components of DXN, HCl, CBz and CP are separated, and the stream SHG contains very little CBz and CP, and is used for high-temperature gas-phase synthesis reactions to generate DXN. Similarly, high-temperature gas-phase reactions use 10 RGibbs modules that generate different Cl atoms to replace DXN. SHG can characterize DXN concentration after the reaction in the high-temperature heat exchange zone.

Figure 6:
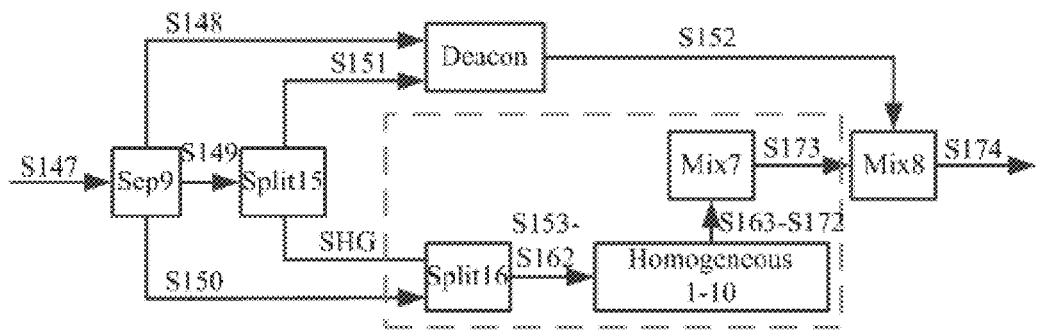
FIG. 6 is a structural diagram of the high temperature heat exchange zone simulation model.
Figure 7:
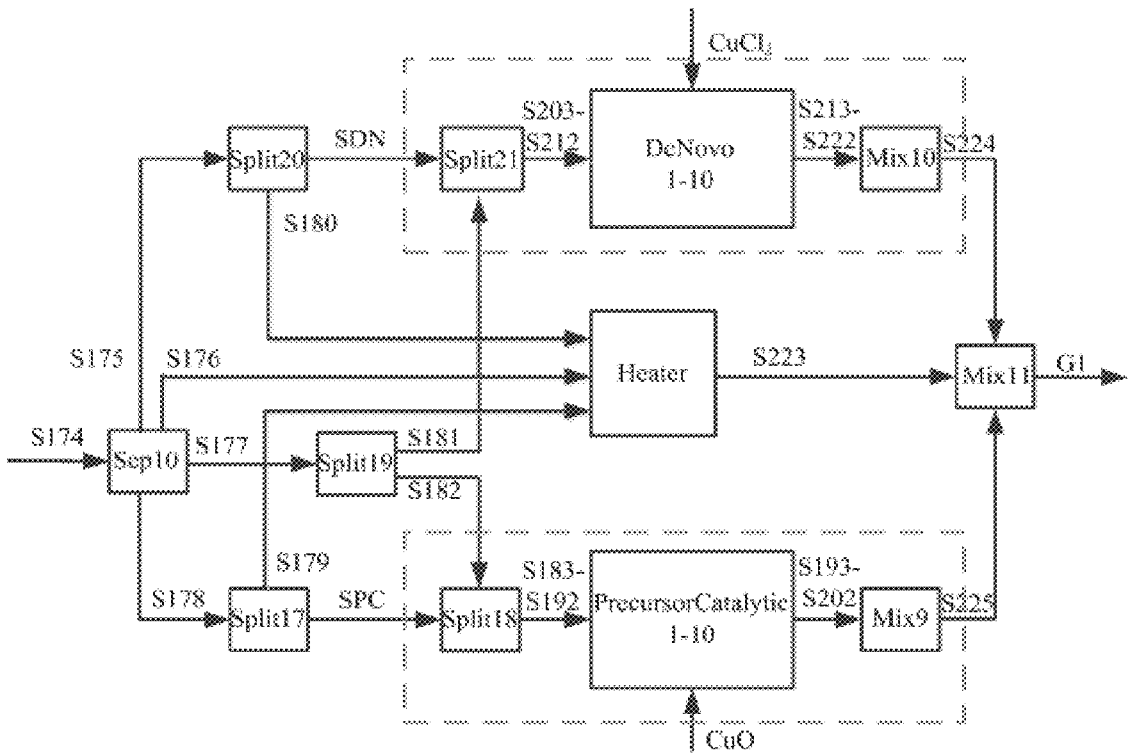
FIG. 7 is the structural diagram of the low temperature heat exchange zone simulation model.

As shown in FIG. 6, the low temperature heat exchange zone includes a Sep10 module, the Mix8 module is connected to the Sep10 module, the Sep10 module is respectively connected to the Split17 module, the Split19 module, the Split20 module and the Heater module, and the Split17 module is connected to the Split18 module and the Heater module, the Split20 module is respectively connected to the Split21 module and the Heater module, the stream that the Split17 module connected to the Split18 module and the Split20 module connected to the Split21 module is the DXN concentration after the reaction in low-temperature heat exchange zone, recorded as SPC and SDN respectively, the Split19 module is connected to the Split18 module and the Split21 module respectively, the Split18 module is connected to the PrecursorCatalytic1-10 module, the PrecursorCatalytic1-10 module is connected to the Mix9 module, and the Split21 module is connected to DeNovo1-10 module, the DeNovo1-10 module is connected to the Mix10 module, the Mix9 module, Mix10 module and Heater module are connected to the Mix11 module, and the DXN concentration at the boiler outlet is output, the DeNovo1-10 module flows into $CuCl_2$, and the PrecursorCatalytic1-10 module flows into CuO; The stream S174 originating from the high-temperature heat exchange zone is divided into streams S175, S176, S177, and S178 by separating DXN from HCl, $Cl_2$, CBz, and CP through Sep10; further, S178 is divided into streams S179 and SPC by Split17. SPC contains small amount CBz and CP, which enters PrecursorCatalytic1-10 to simulate the catalytic reaction of precursors, and at the same time, S175 is divided into stream S180 and SDN by Split20, SDN contains small amount $Cl_2$, which enters DeNovo1-10 to simulate generates DXN from the de novo synthesis reaction. Similarly, the PrecursorCatalytic and DeNovo reactions also use 10 RGibbs reactors each. Finally, the DXN concentration is obtained at the boiler outlet G1. SPC and SDN can characterize the DXN concentration after the reaction in the low-temperature heat exchange zone.

As shown in FIG. 2, the present invention also provides a simulation analysis method for dioxin concentration in furnace of municipal solid waste Incineration process, which includes the following steps:

Step 1: Based on MSWI process and the formation, decomposition and regeneration mechanism of DXN in the furnace, furnace area of the incinerator is divided into solid phase combustion area, gas phase combustion area, high temperature heat exchange area and low temperature heat exchange area through the area division module.

Step 2: According to the actual incinerator equipment parameters, operating parameters and boundary conditions, and the divided area, to simulate the numerical simulation model of the actual DXN emission value range through the numerical simulation module, and use the single factor analysis module to analyze four streams of SPY, SHG, SPC and SDN;

Step 3: Carry out multi-factor orthogonal test analysis through the orthogonal test analysis module according to single factor analysis results and numerical simulation module.

Through single factor analysis module, single factor analysis of the four streams of SPY, SHG, SPC and SDN is carried out, specifically:

In order to explore the influence of the reactant concentration represented by split fraction on DXN concentration at the boiler outlet G1, a single factor analysis was carried out on the four streams of SPY, SHG, SPC and SDN.

Among them, the corresponding reaction temperatures of SPY, SHG, SPC and SDN are expressed as TPY, THG, TPC and TDN, respectively. In order to explore the influence of reaction temperature on the concentration of DXN at G1, single factor analysis was carried out on the reaction temperatures TPY, THG, TPG and TDN. Using "y" to represent the DXN concentration at the G1 flue gas, the relationship between it and the above-mentioned 8 main factors and other factors can be expressed as:

$$y = f_{model}(x_{SPY}, x_{SHG}, x_{SPC}, x_{SDN}, x_{TPY}, x_{THG}, x_{TPG}, x_{TDN}, x_{other}, \dots)$$

Wherein $x_{SPY}$, $x_{SHG}$, $x_{SPC}$, $x_{SDN}$, $x_{TPY}$, $x_{THG}$, $x_{TPC}$, $x_{TDN}$ represent the values of SPY, SHG, SPC, SDN, TPY, THG, TPG and TDN respectively, and $x_{other}$ represents the values of industrial analysis, elemental analysis, primary air volume, secondary air volume and other variables;

Taking $x_{SPY}$ as an example, the result of a single factor analysis can be expressed as:

$$y_{SPY} = f_{model}(x_{SPY}^{var}, x_{SHG}^{fixed}, x_{SPC}^{fixed}, x_{SDN}^{fixed}, x_{TPY}^{fixed}, x_{THG}^{fixed}, x_{TPG}^{fixed}, x_{TDN}^{fixed}, x_{other}^{fixed}, \dots)$$

Wherein $x_{SPY}^{var}$ represents the value of SPY when carrying out single factor analysis, and its range is between $x_{SPY}^{min}$ and $x_{SPY}^{max}$, $x_{SHG}^{fixed}$, $x_{SPC}^{fixed}$, $x_{SDN}^{fixed}$, $x_{TPY}^{fixed}$, $x_{THG}^{fixed}$, $x_{TPG}^{fixed}$ and $lx_{TDN}^{fixed}$ represents the value of TPG and TDN when carrying out $x_{SPY}$ single factor fixed analysis; $x_{other}^{fixed}$ represents the fixed values for variables such as industrial analysis, elemental analysis, primary air volume, and secondary air volume in the simulation.

According to single factor analysis results and data simulation module, the multi-factor orthogonal test analysis is carried out through the orthogonal test analysis module:

Through the analysis of single factor variables, only the influence of different single factors on DXN concentration, PCDFs concentration, PCDDs concentration and the ratio between PCDFs/PCDDs can be obtained. Actual MSWI process is the result of multiple factors. To test the effects of 8 factors including SHG split ratio, SPC split ratio, SDN split ratio, pyrolysis reaction temperature TPY, high temperature gas phase reaction temperature THG, precursor catalytic reaction temperature TPC, and de novo synthesis reaction temperature TDN on the concentration of DXN at G1, a multi-level orthogonal experiment on these factors is conducted, for a certain experiment, its output can be expressed as:

$$y^{design} = f_{model}(x_{SPY}^{design}, x_{SHG}^{design}, x_{SPC}^{design}, x_{SDN}^{design}, x_{TPY}^{design}, x_{THG}^{design}, x_{TPG}^{design}, x_{TDN}^{design}, x_{other}^{fixed}, \dots)$$

Wherein $x_{SPY}^{design}$, $x_{SHG}^{design}$, $x_{SPC}^{design}$, $x_{SDN}^{design}$, $x_{TPY}^{design}$, $x_{THG}^{design}$, $x_{TPG}^{design}$, and $lx_{TDN}^{design}$ respectively represent the design values of SHG, SPC, SDN, TPY, THG, TPG and TDN in the orthogonal experiment analysis, and $x_{other}^{fixed}$ represent the designed value of industrial analysis, elemental analysis, primary air volume, secondary air volume and other variables in the simulation. Using range calculation formula to analyze the importance of each factor, as shown in the formula (1):

$$R_i = f_{max}(\bar{y}_{i1}, \bar{y}_{i2}, \dots, \bar{y}_{ij}) - f_{min}(\bar{y}_{i1}, \bar{y}_{i2}, \dots, \bar{y}_{ij}) \tag{1}$$

Wherein i represents the i-th factor in the orthogonal experiment, j represents the j-th level of the i-th factor, and $$\bar{y}_{ij} = \frac{\sum_{n=1}^{r} y_n^{design}}{r}$$

represents the average value of r experimental data $y^{design}$ at the j-th level of the i-th factor, and r represents the number of occurrences of that level in the experiment.

Taking an incineration power plant in Beijing as an example, the results of industrial analysis and element analysis are shown in Table 1; combined with the site, the relevant settings of primary air and secondary air are shown in Table 2; the settings of split ratio and reaction temperature are shown in Table 3.

TABLE 1 the results of MSW industrial analysis and element analysis

|  | Project | value | Unit |
|---|---|---|---|
| Industrial analysis | Moisture M(ar) | 36.3 | % |
|  | Fixed Carbon FC(d) | 14.16 | % |
|  | Volatiles V(d) | 60.08 | % |
|  | ASH(d) | 25.76 | % |
| Element analysis | C(d) | 47.66 | % |
|  | H(d) | 6.17 | % |
|  | N(d) | 0.33 | % |
|  | Cl(d) | 0.88 | % |
|  | S(d) | 0.17 | % |
|  | O(d) | 19.03 | % |

Note:
"ar" represents received basis, that is, the received status sample is used as basis; "d" represents dry basis, that is, the sample under hypothetical anhydrous state is used as the basis.

TABLE 2 the relevant settings of primary air and secondary air

|  | location | Temperature (° C.) | flux (kg/h) | constitution |
|---|---|---|---|---|
| Primary air | Dry grate | 226.85 | 20688 | $N_2/O_2 = 0.79/0.21$ (Molar fraction) |
|  | Combustion grate 1 | 226.85 | 43962 |  |
|  | Combustion grate 2 | 226.85 | 18102 |  |
|  | burning grate | 226.85 | 5172 |  |
| Secondary air | Front and rear arch of the furnace | 28.65 | 9051 |  |

TABLE 3 the settings of split ratio and reaction temperature

| Module and stream source | Split fraction | Reaction module and temperature name | Temperature (° C.) |
|---|---|---|---|
| Split9-SPY | $1 \times 10^{-4}$ | Pyrolysis-TPY | 850 |
| Split15-SHG | $1 \times 10^{-3}$ | Homogeneous-THG | 650 |

TABLE 3-continued the settings of split ratio and reaction temperature

| Module and stream source | Split fraction | Reaction module and temperature name | Temperature (° C.) |
|---|---|---|---|
| Split17-SPC | $1 \times 10^{-3}$ | PrecursorCatalytic-TPC | 350 |
| Split20-SDN | $1 \times 10^{-7}$ | DeNovo-TDN | 350 |

Figure 9:
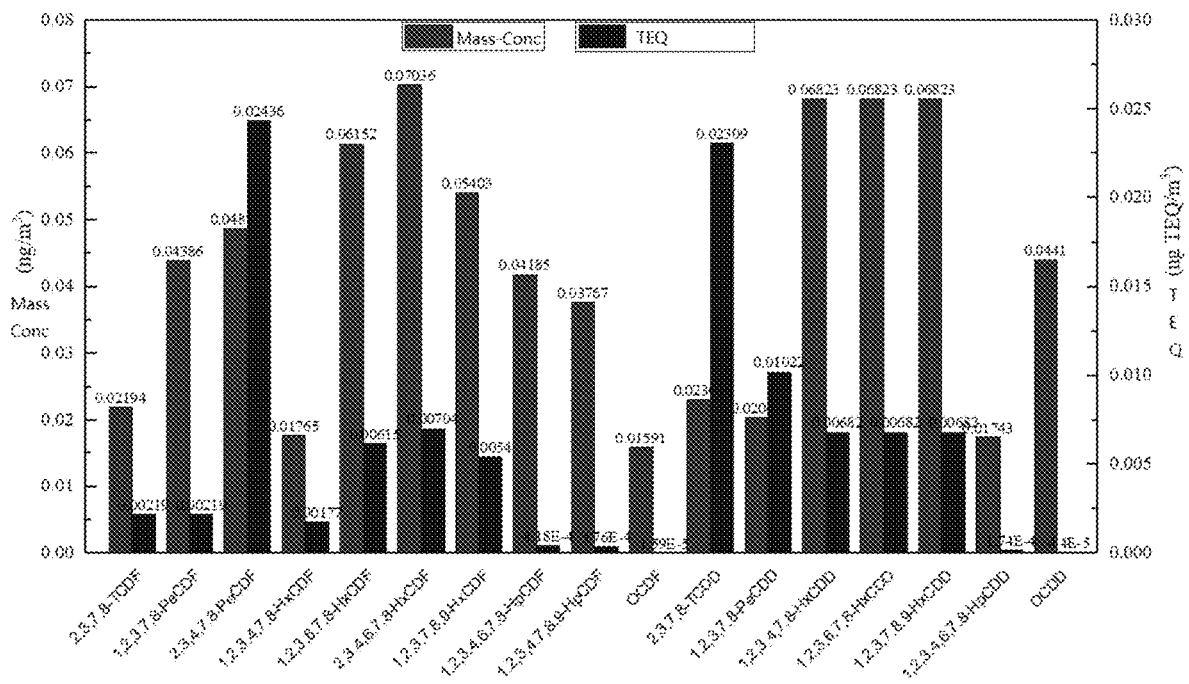
FIG. 9 is a simulation result of DXN concentration at G1.
Figure 10:
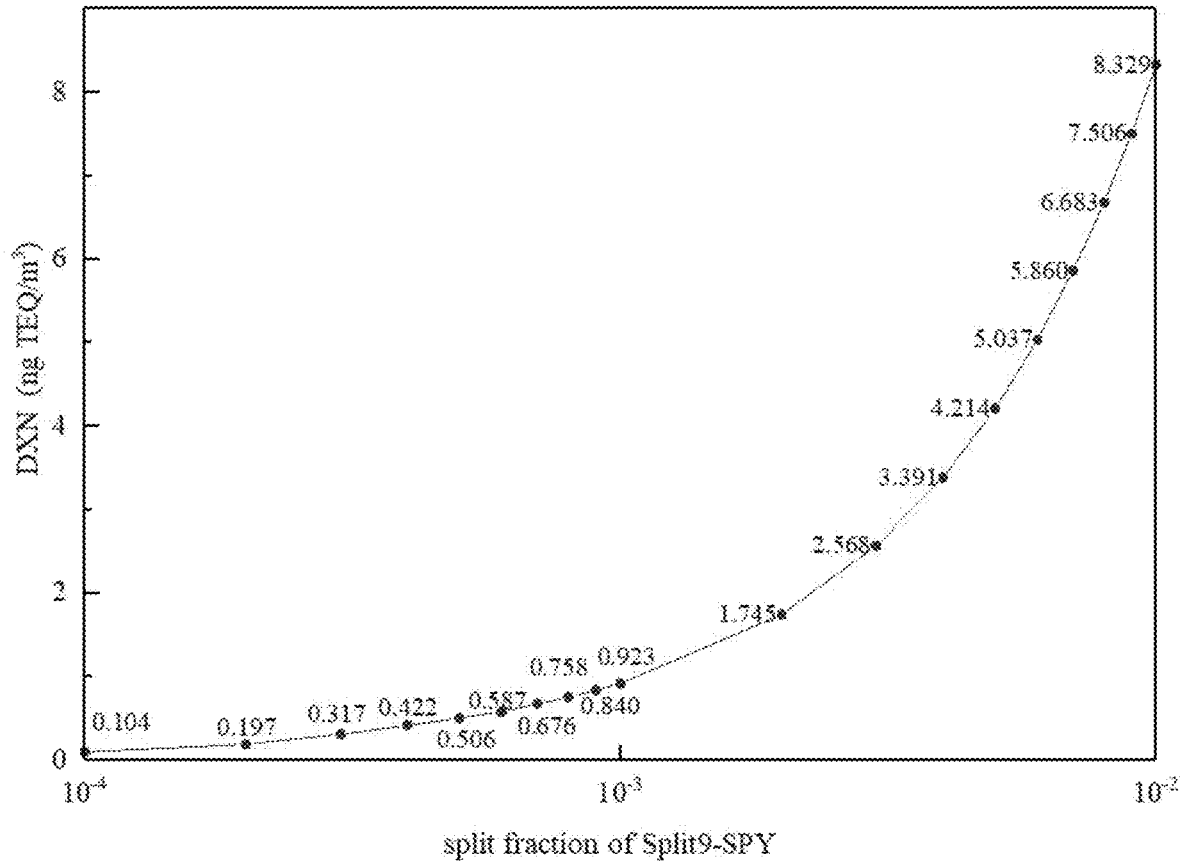
FIG. 10 is the influence of SPY split ratio on DXN concentration.
Figure 11:
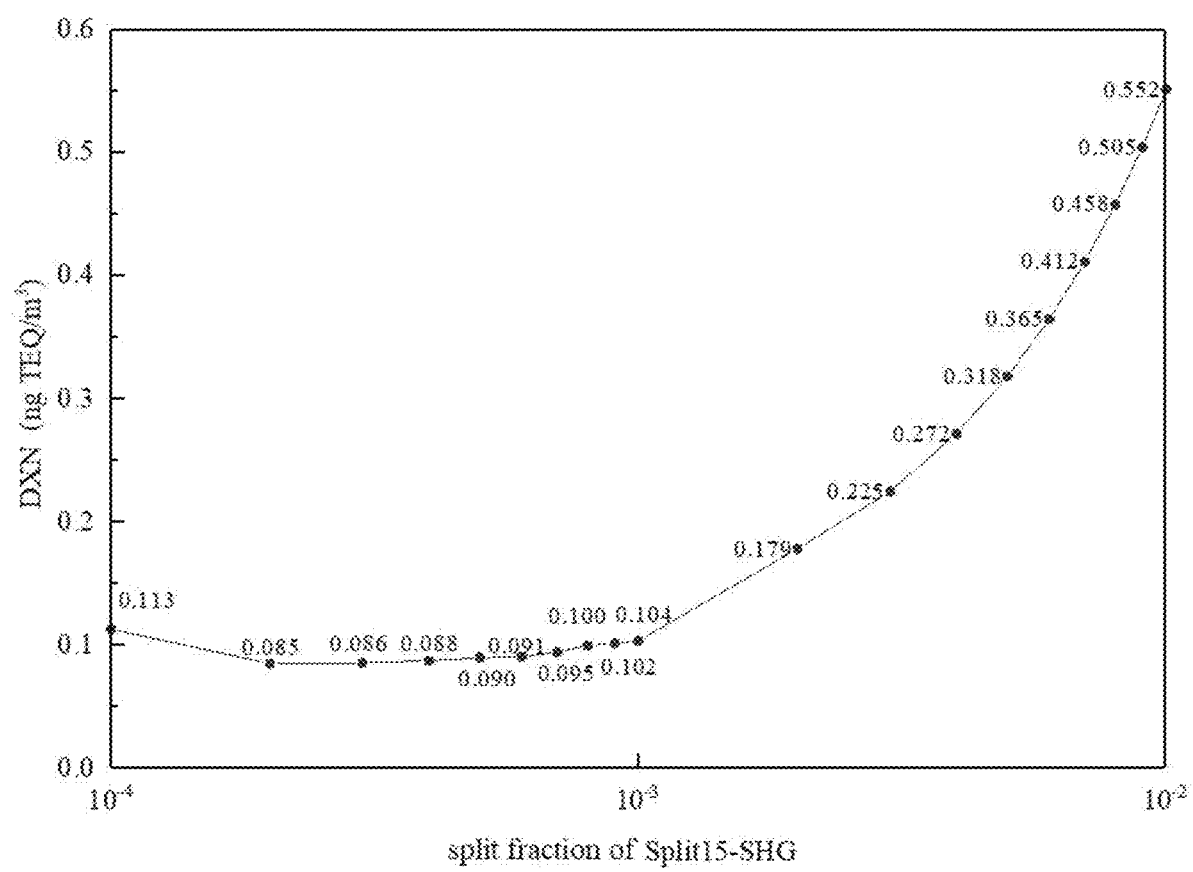
FIG. 11 is the influence of SHG split ratio on DXN concentration.
Figure 12:
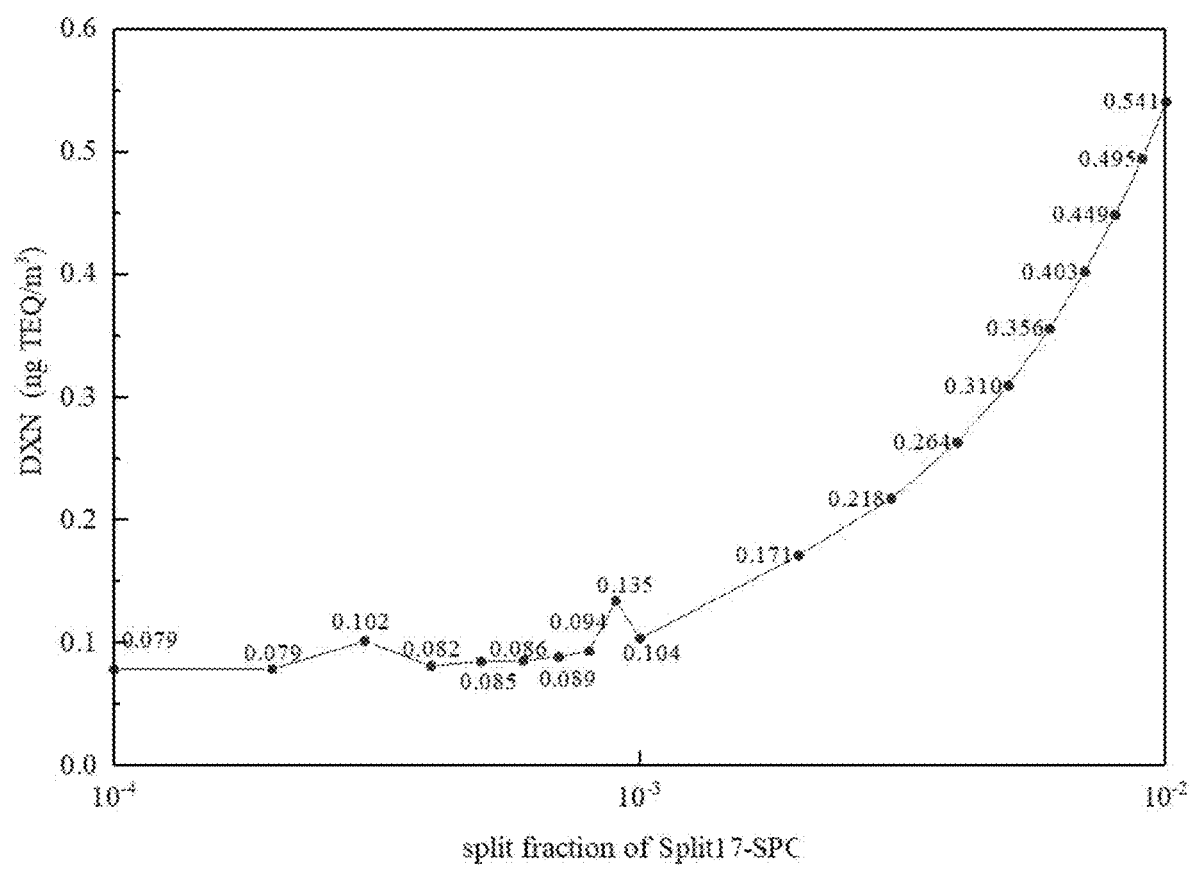
FIG. 12 is the influence of SPC split ratio on DXN concentration.
Figure 13:
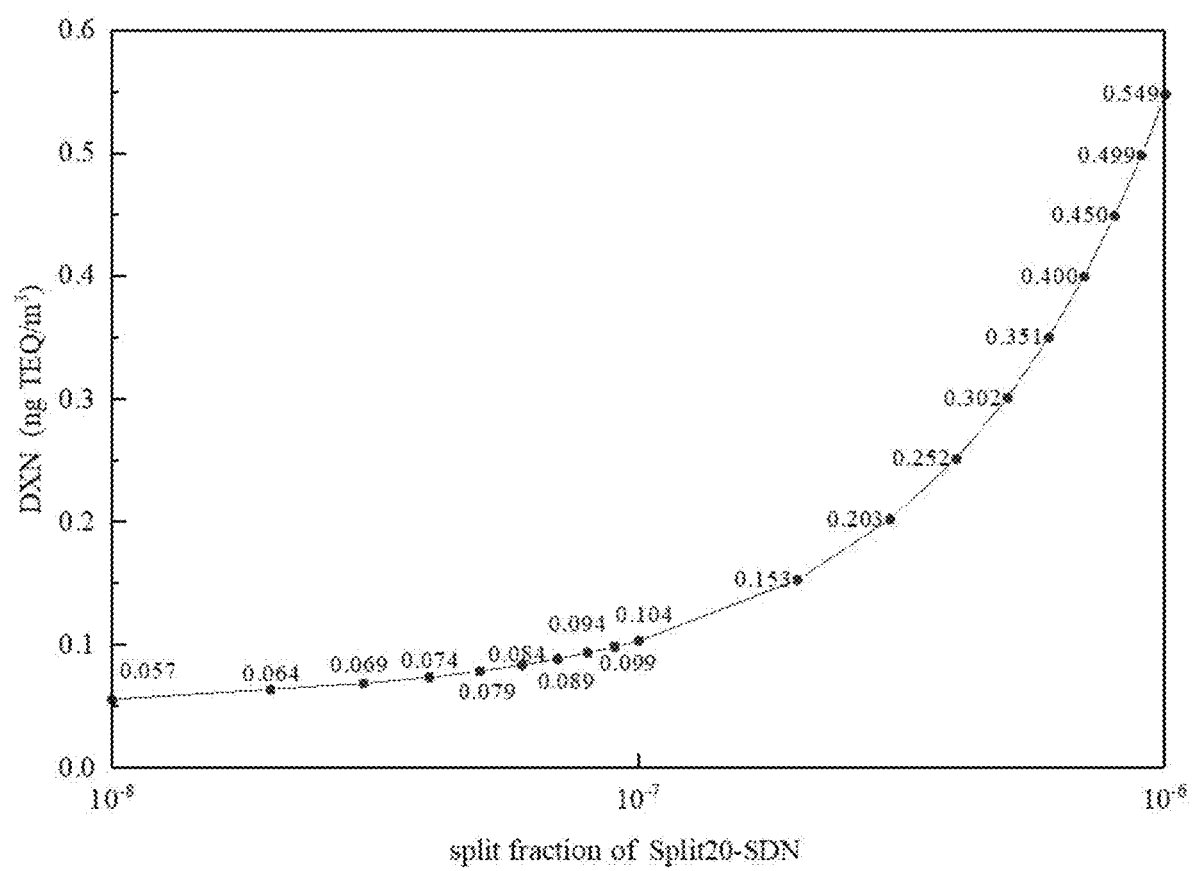
FIG. 13 is the influence of SDN split ratio on DXN concentration.
Figure 14:
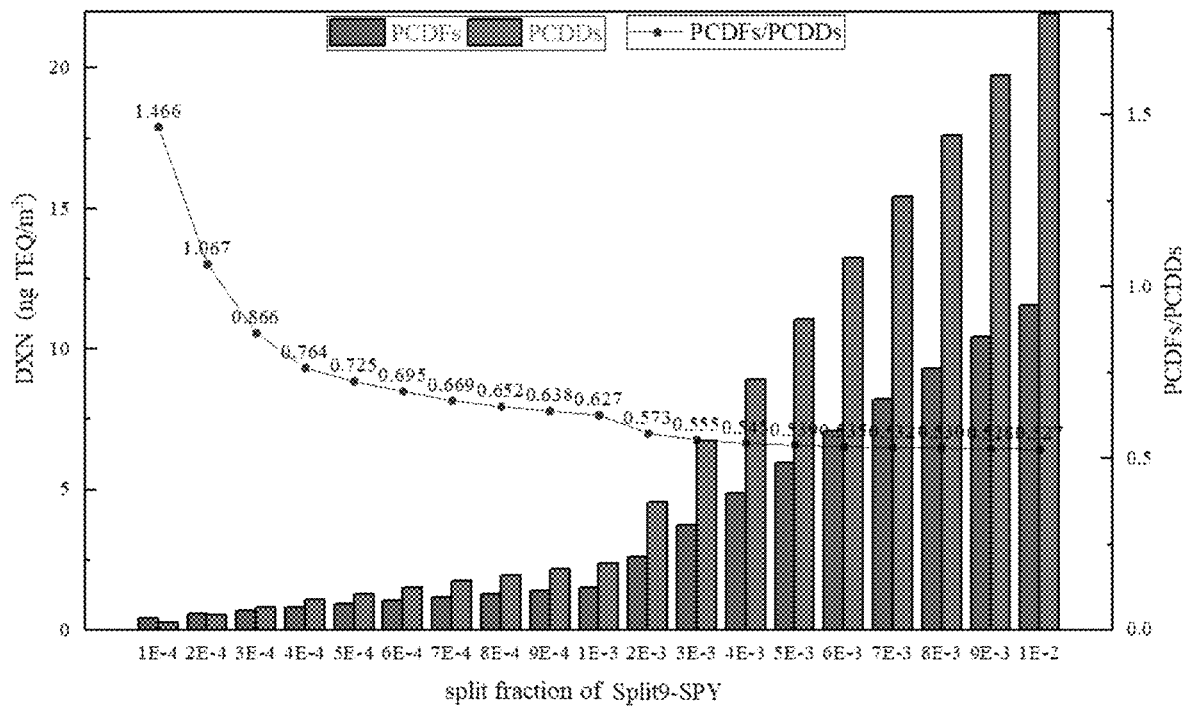
FIG. 14 is the influence of SPY split ratio on the PCDFs and PCDDs concentration and the ratio between PCDFs/PCDDs.
Figure 15:
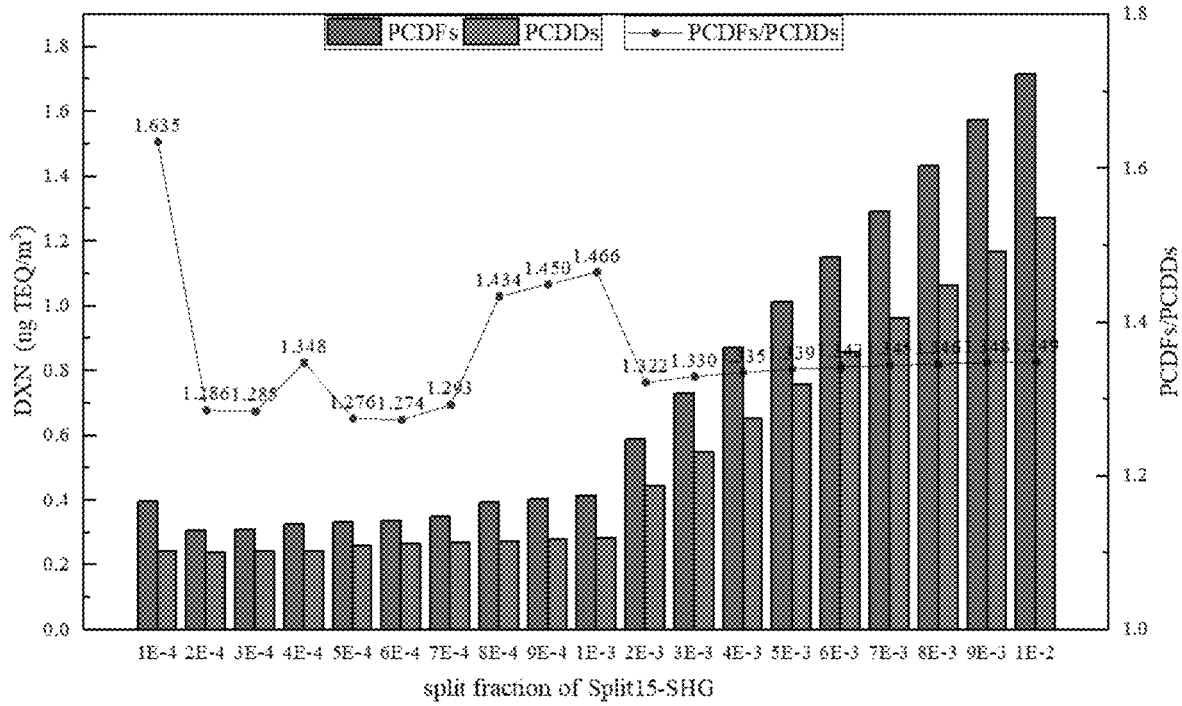
FIG. 15 is the influence of SHG split ratio on the PCDFs and PCDDs concentrations and the ratio between PCDFs/PCDDs.
Figure 16:
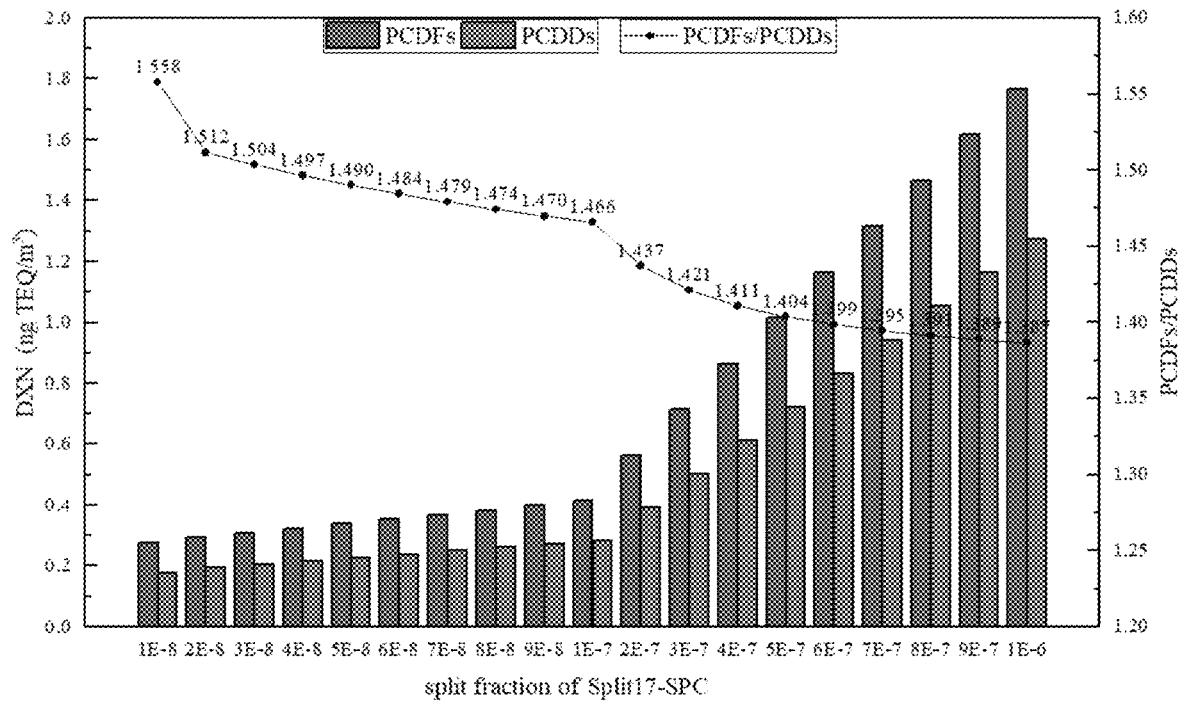
FIG. 16 is the influence of SPC split ratio on the PCDFs and PCDDs concentrations and the ratio between PCDFs/PCDDs.
Figure 17:
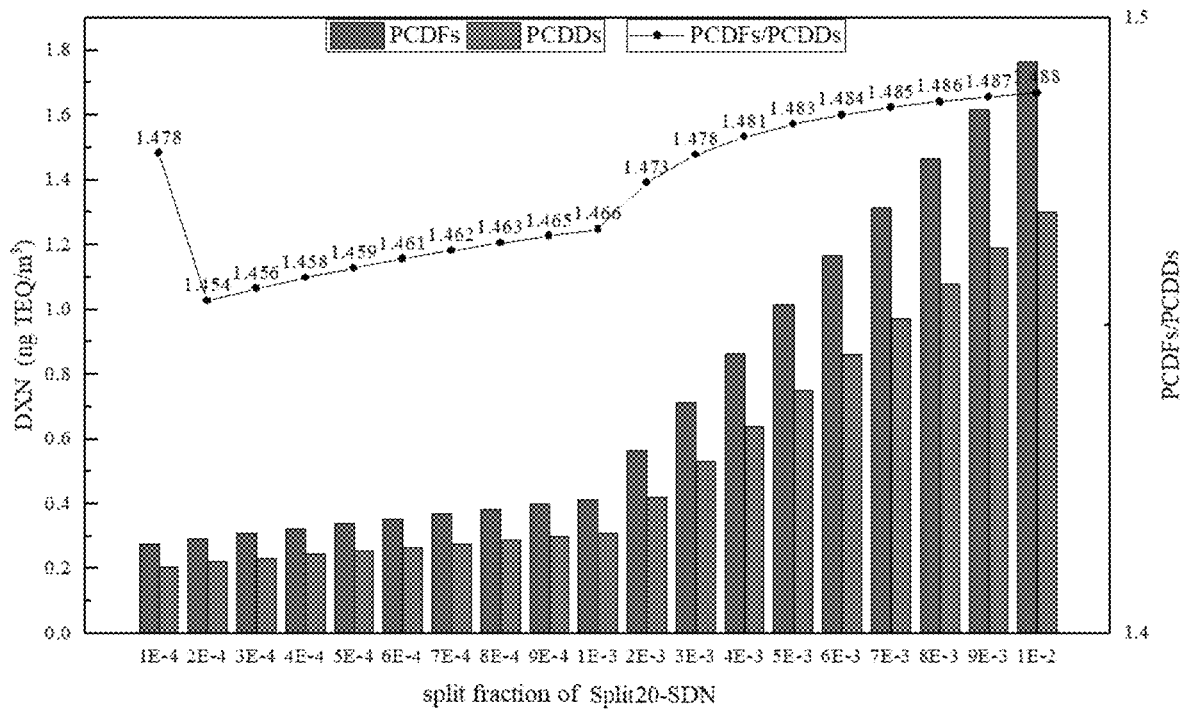
FIG. 17 is the influence of SDN split ratio on the PCDFs and PCDDs concentration and the ratio between PCDFs/PCDDs.
Figure 18:
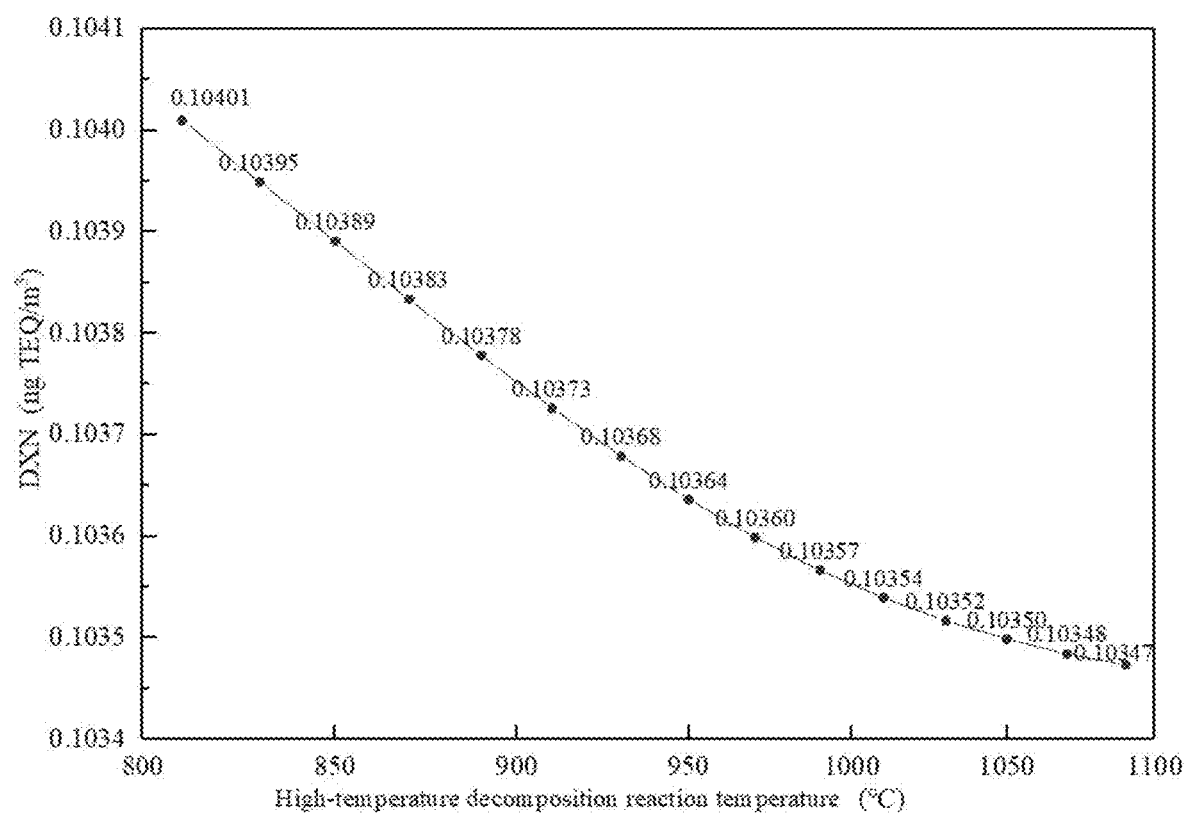
FIG. 18 is the influence of pyrolysis reaction temperature TPY on DXN concentration.
Figure 19:
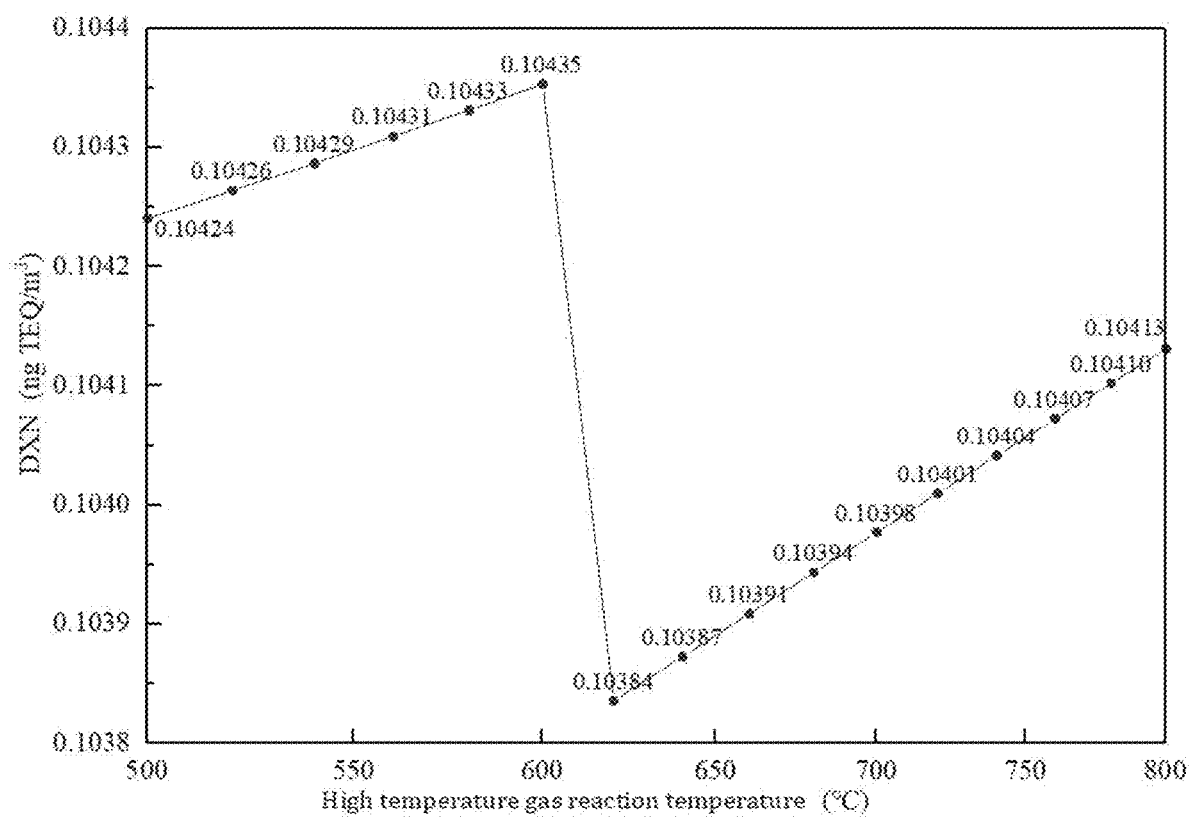
FIG. 19 is the influence of high temperature gas phase reaction temperature THG on DXN concentration.
Figure 20:
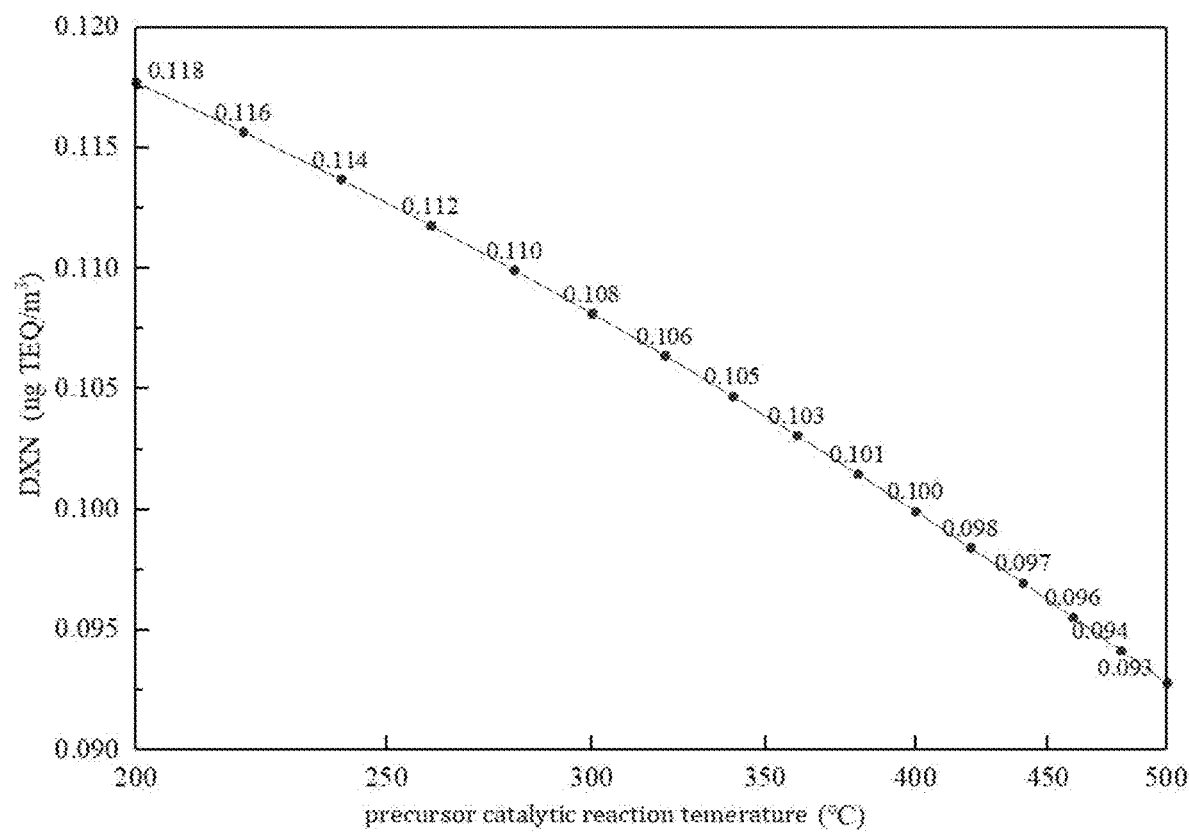
FIG. 20 is the influence of precursor catalytic reaction temperature TPC on DXN concentration.
Figure 21:
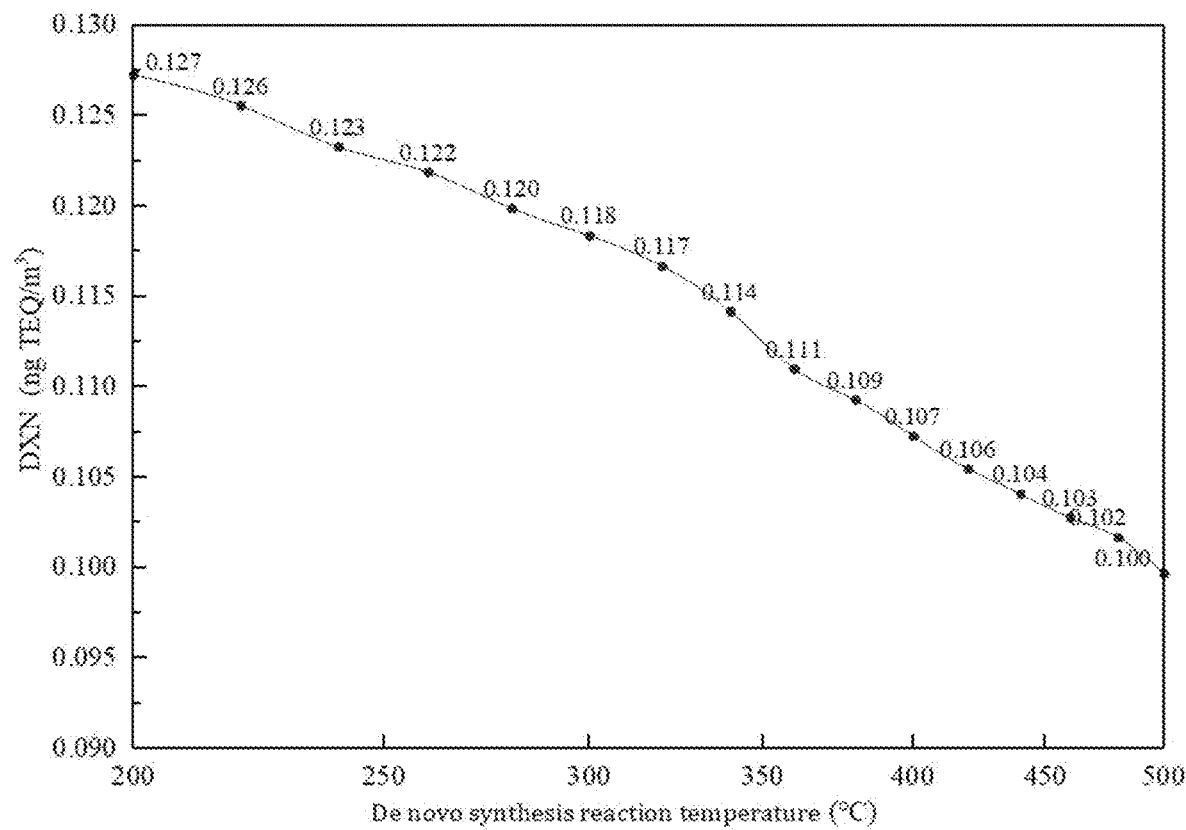
FIG. 21 is the influence of de novo synthesis reaction temperature TDN on DXN concentration.

Simulation is carried out by the numerical simulation module, and the concentration of 17 kinds of DXN congeners at G1 is obtained, as shown in FIG. 9, the toxic equivalent concentration of 17 kinds of DXN congeners is 0.1039 ng TEQ/m$^3$, the contribution of 2, 3, 7, 8-T4CDD and 2, 3, 4, 7, 8-P5CDF to the total TEQ is relatively high, the total mass concentration of 17 DXN congeners is 0.7233 ng/m$^3$, the mass concentration of 6-chlorinated PCDD/Fs is the highest, and the mass concentration of PCDFs and PCDDs are 0.4135 ng/m and 0.3098 ng/m respectively, which are close to the upper limit of the actual emission at G1.

Single factor analysis was carried out on 4 streams of SPY, SHG, SPC and SDN to determine their influence on the concentration of DXN at boiler outlet G1, where x axis represents the fractional distribution rate in logarithmic form with base 10, as shown in FIG. 10-13, the concentration of DXN increases with the increase of split fraction, among which: the concentration of DXN represented by SPY without pyrolysis has a great influence on the concentration of DXN at G1, the concentration of DXN represented by SHG and SPC which is represents the precursors change in concentration has relatively little effect on the concentration of DXN at G1. The maximum concentration of DXN in the figure is less than 1 ng TEQ/m$^3$. The concentration range of de novo synthesis Cl$_2$ represented by SDN is smaller than that of SHG and SPC, but it affects G1 as same order as SHG and SPC, which may be due to the fact that de novo synthesis is the main way to generate DXN, that is, low concentration of Cl$_2$ can also generate higher concentration of DXN.

The influence of the shunt fraction at SPY, SHG, SPC and SDN on the concentration of PCDDs, PCDFs and the ratio of PCDFs/PCDDs is shown in FIG. 14-17, wherein: in the gas phase combustion DXN decomposition process, the ratio of PCDFs/PCDDs gradually decreased with the increase of SPY fraction, from 1.466 to 0.527, indicating that PCDDs were easier to decompose; in the high temperature gas phase reaction, the ratio was greater than 1 with small change; in the catalytic reaction of precursors, the ratio of PCDFs/PCDDs is from 1.588 to 1.387, although it gradually decreases but is still greater than 1, the reason is that the concentration of generated PCDDs increases with the increase of the concentration of precursors; in the de novo synthesis reaction, the concentration of PCDFs and PCDDs increased with the increase of SDN split fraction, and the ratio of PCDFs/PCDDs also showed a trend of first decreasing and then increasing. A ratio greater than 1 indicated that the concentration of PCDFs was greater than that of PCDDs, that is, the de novo synthesis was dominated by the formation of PCDFs.

In order to explore the effect of reaction temperature on the concentration of DXN at G1, a single factor analysis was performed on the reaction temperature of the four modules of Pyrolysis, Homogeneous, PrecursorCatalytic and DeNovo, and the results are shown in FIG. 18-21.

It can be seen from FIG. 18-21 that the DXN concentrations represented by the four curves all change within a small range. Among them, the gas phase combustion DXN decomposition process conforms to the higher the temperature, the higher the decomposition rate. In the high temperature gas phase reaction, the DXN concentration is between 2 temperature zones shows an increasing trend, and the highest concentration of DXN is produced near 600° C. In the catalytic reaction of precursors and the de novo synthesis reaction, the concentration of DXN gradually decreases with the increase of temperature, so the two reactions are more inclined to low temperature reactions.

In order to investigate the SPY split fraction (A), SHG split fraction (B), SPC split fraction (C), SDN split fraction (D), pyrolysis reaction temperature TPY (E), high temperature gas phase reaction temperature THG (F), precursor catalytic reaction temperature TPC(G), and de novo synthesis reaction temperature TDN(H), a total of 8 factors who affected the concentration of DXN at G1, a three-level eight-factor orthogonal experiment was carried out. The selection of factor levels is shown in table 4, and the results of orthogonal experiments are shown in table 5.

TABLE 4

| | factor levels | | | | | | | |
|---|---|---|---|---|---|---|---|---|
| level | A | B | C | D | E/° C. | F/° C. | G/° C. | H/° C. |
| 1 | 5E−5 | 5E−4 | 5E−4 | 5E−8 | 800 | 500 | 200 | 200 |
| 2 | 1E−4 | 1E−3 | 1E−3 | 1E−7 | 850 | 650 | 350 | 350 |
| 3 | 1.5E−4 | 1.5E−3 | 1.5E−3 | 1.5E−7 | 900 | 800 | 500 | 500 |

TABLE 5

| | the schemas and results of orthogonal experiments | | | | | | | | | | | |
|---|---|---|---|---|---|---|---|---|---|---|---|---|
| sample | A | B | C | D | E | F | G | H | DXN ng TEQ/m$^3$ | PCDFs ng/m$^3$ | PCDDs ng/m$^3$ | PCDFs/ PCDDs |
| 1 | 1 | 1 | 1 | 1 | 1 | 1 | 1 | 1 | 0.0578 | 0.1759 | 0.1295 | 1.3579 |
| 2 | 1 | 1 | 1 | 1 | 2 | 2 | 2 | 2 | 0.0353 | 0.1343 | 0.0984 | 1.3650 |
| 3 | 1 | 1 | 1 | 1 | 3 | 3 | 3 | 3 | 0.0286 | 0.1087 | 0.0793 | 1.3700 |
| . | . | . | . | . | . | . | . | . | . | . | . | . |
| . | . | . | . | . | . | . | . | . | . | . | . | . |

TABLE 5-continued the schemas and results of orthogonal experiments

| sample | A | B | C | D | E | F | G | H | DXN ng TEQ/m$^3$ | PCDFs ng/m$^3$ | PCDDs ng/m$^3$ | PCDFs/ PCDDs |
|---|---|---|---|---|---|---|---|---|---|---|---|---|
| . | . | . | . | . | . | . | . | . | . | . | . | . |
| 25 | 3 | 3 | 2 | 1 | 1 | 3 | 2 | 3 | 0.1395 | 0.4210 | 0.4345 | 0.9688 |
| 26 | 3 | 3 | 2 | 1 | 2 | 1 | 3 | 1 | 0.1532 | 0.5059 | 0.4225 | 1.1974 |
| 27 | 3 | 3 | 2 | 1 | 3 | 2 | 1 | 2 | 0.1740 | 0.6211 | 0.4419 | 1.4055 |

Through orthogonal experiment and analysis of experimental results, range analysis results are obtained and shown in Table 6.

TABLE 6

Range analysis

| Index | A | B | C | D | E | F | G | H |
|---|---|---|---|---|---|---|---|---|
| DXN concentration | | | | | | | | |
| Range R | 0.0301 | 0.0632 | 0.0609 | 0.0502 | 0.0066 | 0.0028 | 0.0373 | 0.0323 |
| Primary and secondary order | | B > C > D > G > H > A > E > F | | | | | | |
| Optimal level | A$_1$ | B$_1$ | C$_1$ | D$_1$ | E$_2$ | F$_2$ | G$_3$ | H$_3$ |
| PCDFs concentration | | | | | | | | |
| Range R | 0.0896 | 0.1657 | 0.1423 | 0.1308 | 0.0301 | 0.0266 | 0.1415 | 0.124 |
| Primary and secondary order | | B > C > G > D > H > A > E > F | | | | | | |
| Optimal level | A$_1$ | B$_1$ | C$_1$ | D$_1$ | E$_1$ | F$_3$ | G$_3$ | H$_3$ |
| PCDDs concentration | | | | | | | | |
| Range R | 0.1573 | 0.1331 | 0.1254 | 0.1125 | 0.0348 | 0.0287 | 0.0709 | 0.08 |
| Primary and secondary order | | A > B > C > D > H > G > E > F | | | | | | |
| Optimal level | A$_1$ | B$_1$ | C$_1$ | D$_1$ | E$_3$ | F$_1$ | G$_3$ | H$_3$ |
| PCDFs/PCDDs | | | | | | | | |
| Range R | 0.436 | 0.158 | 0.148 | 0.163 | 0.107 | 0.208 | 0.208 | 0.213 |
| Primary and secondary order | | A > H > G > F > D > B > C > E | | | | | | |
| Optimal level | — | — | — | — | — | — | — | — |

Note:
"—" indicates that the index is not counted because it cannot be judged by the extreme value.

It can be seen from Table 6:
(1) The effect of factor B on DXN concentration at G1 is the top. In the experimental range, the increase of SHG split fraction leads to an increase in the concentration of precursors involved in high-temperature gas phase reaction, which has a great impact on DXN concentration at the furnace outlet. This is inconsistent with Shuab's conclusion that the amount of DXN produced by high-temperature gas phase reaction is very small and is not the main source of DXN produced by incineration. The possible reason is that the third level of factor B is set too large. The influence of factors C and D on the concentration of DXN at G1 occupies the second and third places respectively, indicating that the concentration of reactants in the low temperature heat exchange zone also has a greater influence on it. Factors G and H are behind D, indicating that the reaction temperature in the low-temperature heterogeneous heat exchange zone will also have an impact. The possible reason for the lower ranking of factors A and E is that the decomposition of DXN in the gas phase combustion zone is relatively complete. Factor F occupies the last position, indicating that the high-temperature heat exchange zone is not the main reaction temperature range for the formation of DXN in the experiment. In actual conditions, reasonable process operation should be carried out to make more DXN and precursors burn and decompose in the furnace, which is in line with the 3T+E principle widely used in the current MSWI process; Rapid cooling should be used to shortens the reaction time to generate the DXN reaction. In this orthogonal experiment, the optimal combination is B1C1D1G3H3A1E2F2, and the obtained DXN toxic equivalent concentration is 0.0286 ng TEQ/m$^3$ with the corresponding values ($5\times10^{-3}$, $5\times10^{-3}$, $5\times10^{-8}$, 500, 500, $5\times10^{-6}$, 850, 650).

(2) Factor A has the first influence on PCDFs concentration, and factor B has the first influence on PCDDs concentration, indicating that the DXN concentration and precursors which not decomposed by pyrolysis will have a great impact on the concentration of PCDFs and PCDDs. Factors C, D, G, and H rank in the middle, indicating that the concentration of reactants and reaction temperature in the low-temperature heat exchange zone have certain effects on the concentrations of PCDFs and PCDDs. In this orthogonal experiment, the optimal combinations for PCDFs and PCDDs are B1C$_1$G3D1H3A1E1F3 and A1B1C$_1$D1H3G3E3F1 respectively, and the the mass concentrations of PCDFs and PCDDs are 0.1087 ng/m 3 and 0.0793 ng/m³ respectively with the corresponding values ($5\times10^{-4}$, $5\times10^{-4}$, 500, $5\times10^{-8}$, 500, $5\times10^{-5}$, 800, 800) and ($5\times10^{-5}$, $5\times10^{-4}$, $5\times10^{-4}$, $5\times10^{-8}$, 500, 500, 900, 500).

(3) Factor A has the most important influence on the ratio of PCDFs/PCDDs, followed by factors H, G and F. It can be seen that the concentration of undecomposed DXN in the gas phase combustion zone is the main factor affecting the ratio of PCDFs/PCDDs; if the decomposition of DXN in gas phase combustion is relatively complete, the temperature is the main factor affecting the ratio of PCDFs/PCDDs.

According to the above process, it is concluded that:

(1) The mechanism of DXN formation, decomposition and regeneration in the incinerator was analyzed combined with the actual process flow of a MSWI power plant, and it was divided into four areas: solid phase combustion area, gas phase combustion area, high temperature heat exchange area and low temperature heat exchange area.

(2) Establish a numerical simulation model for DXN in the incinerator, which can reasonably predict the results of the MSWI process, and the simulation results are basically consistent with the actual data, indicating the effectiveness of the numerical simulation model.

(3) Study the influence of single factor changes on the DXN concentration, PCDFs concentration, PCDDs concentration and PCDFs/PCDDs ratio at the boiler outlet G1, where: the DXN concentration increases with the increase of the split ratio, and decreases with the increase of the temperature (The reaction temperature at high temperature gas phase is opposite to it).

(4) Based on the orthogonal experiment and range analysis, the influence of 8 factors on the concentration of DXN, the concentration of PCDFs, the concentration of PCDDs and the ratio of PCDFs/PCDDs was studied. The results indicate that the concentration of reactants can affect DXN concentration more than reaction temperature, and the change of temperature is more likely to cause the change of PCDFs/PCDDs ratio. The optimal parameter combination can be obtained by combining 8 factors. This study provides a theoretical reference for reducing the concentration of DXN emissions at G1.

The present invention provides a simulation analysis system and method for dioxin concentration in a furnace during solid waste incineration. The system includes an area division module, a numerical simulation module, a single factor analysis module and an orthogonal test analysis module. The method includes a process based on MSWI and the formation, decomposition and regeneration mechanism of DXN in the furnace, the furnace area of the incinerator is divided into solid phase combustion area, gas phase combustion area, high temperature heat exchange area and low temperature heat exchange area through the area division module. According to equipment parameters, operating parameters and boundary conditions of the actual incinerator and the divided areas to simulated through the numerical simulation model of the actual DXN emission value range through the data simulation module, and the single factor analysis is performed on the four streams of SPY, SHG, SPC and SDN through the single factor analysis module, according to the single factor analysis results and the data simulation module, the multi-factor orthogonal test analysis is carried out through the orthogonal test analysis module; through the simulation between models, and comparing it with the actual data, the results are basically consistent, indicating the effectiveness of the numerical simulation model is demonstrated, which can effectively analyze and simulate the mechanism of DXN generation, combustion and regeneration in the MSWI process incinerator, and provide a reference for reducing DXN concentration at the exit of waste heat boiler.

In the invention, specific examples have been used to illustrate the principle and implementation of the present invention. The description of the above embodiments is only used to help understand the method of the present invention and its core idea; meanwhile, for those of ordinary skill in the art, according to the thoughts of present invention, there will be changes in specific implementation methods and application ranges. In summary, the contents of this specification should not be construed as limiting the present invention.

We claim:

1. A simulation analysis system for dioxin concentration in a furnace during a municipal solid waste incineration process, comprising: an area division module, a numerical simulation module, a single factor analysis module and an orthogonal test analysis module, and the area division module is connected to the numerical simulation module, the numerical simulation module is connected to the single factor analysis module, the single factor analysis module includes the orthogonal test analysis module, and the area division module is used to divide the furnace area of the incinerator, the numerical simulation module is used to model and simulate the divided regions, the single factor analysis module is used to perform single factor analysis according to the output of the numerical simulation module, and the orthogonal test analysis module is used to perform single factor analysis according to the output of the numerical simulation module and carry out orthogonal test analysis;

the numerical simulation module includes a solid phase combustion zone simulation model, a gas phase combustion zone simulation model, a high temperature heat exchange zone simulation model, and a low temperature heat exchange zone simulation model, the solid phase combustion zone simulation model is connected to the gas phase combustion zone simulation model, the gas phase combustion zone simulation model is connected to the high temperature heat exchange zone simulation model, the high temperature heat exchange zone simulation model is connected to the low temperature heat exchange zone simulation model.

2. The simulation analysis system for dioxin concentration in a furnace during a municipal solid waste incineration process according to claim 1, comprising: the solid phase combustion zone simulation model, the gas phase combustion zone simulation model, the high temperature heat exchange zone simulation model, and the low temperature heat exchange zone simulation model are composed of RStoic module, RGibbs module, RYield module, Sep module, Fsplit module and Mixer module, wherein RStoic module comprises Dry module and Deacon module, and RGibbs module comprises CombustionA1-A10 module, CombustionB1-B10 module, CombustionC1-C10 module, CombustionD1-D10 module, Pyrolysis1-10 module, Homogeneous1-10 module, PrecursorCatalytic1-10 modules and DeNovo1-10 modules, the RYield module includes a DryGrate module, a BurnGrate1 module, a BurnGrate2 module and a BurnoutGrate module, the Sep module includes a Sep1-Sep10 module, the Fsplit module includes a Split1-Split21 module, and the Mixer module includes Mix1-Mix11 modules;

the Dry module is used to reduce the water content of MSW, the Deacon module is used to carry out Deacon reaction, and the CombustionA1-A10 module, CombustionB1-B10 module, CombustionC1-C10 module, CombustionD1-D10 module are used to carry out solid-phase combustion, producing DXN, the Pyrolysis1-10 module is used for gas phase combustion, decomposition DXN, the Homogeneous1-10 module is used for high temperature gas phase reaction, the PrecursorCatalytic1-10 module is used for precursor catalytic reaction, the DeNovo1-10 module for de novo synthesis reaction, the DryGrate module, BurnGrate1 module, BurnGrate2 module and BurnoutGrate module are used to convert MSW into identifiable conventional components, simulated volatile analysis, and the Sep1-Sep10 module is used for component separation, the Split1-Split21 modules are used to split streams and the Mix1-Mix11 modules are used to mix streams.

3. The simulation analysis system for dioxin concentration in a furnace during a municipal solid waste incineration process according to claim 2, comprising: the solid-phase combustion zone simulation model includes a Dry module, MSW is input into the Dry module, the Dry module is respectively connected to the Split1, Split2 and Split3 modules, and the Split1 module is respectively connected to the DryGrate module, BurnGrate1 module, BurnGrate2 module and BurnoutGrate module, the DryGrate module, BurnGrate1 module, BurnGrate2 module and BurnoutGrate module are respectively connected to Sep4, Sep5, Sep6 and Sep7 modules, the Split3 module is connected to the Dry module and the DryGrate module respectively, and the Split2 module is respectively Connect Sep4, Sep5, Sep6 and Sep7 modules, the DryGrate module connects the BurnGrate1 module through Sep1, the BurnGrate1 module connects the BurnGrate2 module through Sep2, the BurnGrate2 module connects the BurnoutGrate module through the Sep3 module, and the Sep4, Sep5, Sep6 and Sep7 modules are respectively connected to the CombustionA1-A10 module, CombustionB1-B10 module, CombustionC1-C10 module, CombustionD1-D10 module through the Split4, Split5, Split6, Split7 modules, the CombustionA1-A10 module, CombustionB1-B10 module, CombustionC1-C10 module, CombustionD1-D10 module are respectively connected to Mix5 module through Mix1, Mix2, Mix3 and Mix4 modules.

4. The simulation analysis system for dioxin concentration in a furnace during a municipal solid waste incineration process according to claim 3, comprising: the gas-phase combustion zone simulation model includes a Sep8 module, the Mix5 module is connected to the Sep8 module, and the Sep8 module is respectively connected to the Split8, Split9, Split11, Split13 modules and the Pyrolysis6 module, and the Split8 modules are respectively connect Split9, Split11, Split13 module and Pyrolysis6 module, Split9 module connects Split10 module and Pyrolysis6 module respectively, and wherein, the stream that Split9 module connects Split10 module is the contained DXN concentration after gas phase combustion zone reaction, which is recorded for SPY, the Split10 module is connected to the Pyrolysis1-5 module, the Split11 module is connected to the Split12 module and the Pyrolysis6 module, the Split12 module is connected to the Pyrolysis7-8 module, the Split13 module is connected to the Pyrolysis6 module and the Split14 module, and the Split14 module is connected to the Pyrolysis9-10 module, and the Pyrolysis1-5 module, the Pyrolysis6 module, the Pyrolysis7-8 module, and the Pyrolysis9-10 module are connected to the Mix6 module.

5. The simulation analysis system for dioxin concentration in a furnace during a municipal solid waste Incineration process according to claim 4, comprising: the high temperature heat exchange zone includes a Sep9 module, the Mix6 module is connected to the Sep9 module, the Sep9 module is respectively connected to the Deacon module, the Split15 module and the Split16 module, and the Split15 module is respectively connected to the Deacon module and the Split16 module, wherein, the stream of the Split15 module connected to the Split16 module is the DXN concentration after the reaction in the high-temperature heat exchange zone, denoted as SHG, the Split16 module is connected to the Homogeneous1-10 module, and the Homogeneous1-10 module is connected to the Mix7 module, the Deacon module and the Mix7 module are connected to the Mix8 module.

6. The simulation analysis system for dioxin concentration in a furnace during a municipal solid waste Incineration process according to claim 5, comprising: the low temperature heat exchange zone includes a Sep10 module, the Mix8 module is connected to the Sep10 module, the Sep10 module is respectively connected to the Split17 module, the Split19 module, the Split20 module and the Heater module, and the Split17 module is respectively connected to the Split18 module and the Heater module, the Split20 module is respectively connected to the Split21 module and the Heater module, the Split17 module is connected to the stream of the Split18 module, the Split20 module is connected to the stream of the Split21 module, which is the concentration of DXN after the reaction in the low temperature heat exchange zone, recorded as SPC and SDN, respectively, the Split19 module is connected to the Split18 module and the Split21 module, the Split18 module is connected to the PrecursorCatalytic1-10 module, the PrecursorCatalytic1-10 module is connected to the Mix9 module, and the Split21 module is connected to the DeNovo1-10 modules, the DeNovo1-10 module is connected to the Mix10 module, the Mix9 module, Mix10 module and Heater module are connected to the Mix11 module to output the DXN concentration at the boiler outlet.

7. A simulation analysis method for dioxin concentration in a furnace during a municipal solid waste incineration process, which is applied to the simulation analysis system for dioxin concentration in a furnace during a municipal solid waste incineration process according to claim 1, including the following steps:
Step 1: based on the MSWI process and the formation, decomposition and regeneration mechanism of DXN in the furnace, the furnace area of the incinerator is divided into solid phase combustion area, gas phase combustion area, high temperature heat exchange area and low temperature exchange area through the area division module;
Step 2: according to the actual incinerator equipment parameters, operating parameters and boundary conditions, and the divided area, to simulate the numerical simulation model of the actual DXN emission value range through the data simulation module, and use the single factor analysis module to analyze SPY, SHG, SPC and SDN Single factor analysis of four streams;
Step 3: carry out multi-factor orthogonal test analysis through the orthogonal test analysis module according to the single factor analysis results and the data simulation module.

* * * * *